(12) United States Patent
Shields et al.

(10) Patent No.: US 7,442,193 B2
(45) Date of Patent: Oct. 28, 2008

(54) ELECTRICALLY CONDUCTIVE/INSULATIVE OVER-SHOE FOR TISSUE FUSION

(75) Inventors: Chelsea Shields, Boulder, CO (US); Edward C. Meagher, Greenlawn, NY (US)

(73) Assignee: Covidien AG, Neuhausen am Rheinfall (CH)

( * ) Notice: Subject to any disclaimer, the term of this patent is extended or adjusted under 35 U.S.C. 154(b) by 840 days.

(21) Appl. No.: 10/718,379

(22) Filed: Nov. 20, 2003

(65) Prior Publication Data
US 2005/0113828 A1    May 26, 2005

(51) Int. Cl.
*A61B 18/12* (2006.01)
(52) U.S. Cl. .......................... 606/49; 606/51
(58) Field of Classification Search ............. 606/49–52, 606/205; 7/121
See application file for complete search history.

(56) References Cited

U.S. PATENT DOCUMENTS

| | | | |
|---|---|---|---|
| 371,664 | A | 10/1887 | Brannan et al. |
| 702,472 | A | 6/1902 | Pignolet |
| 728,883 | A | 5/1903 | Downes |
| 1,586,645 | A | 6/1926 | Bierman |
| 2,002,594 | A | 5/1935 | Wappler et al. |
| 2,011,169 | A | 8/1935 | Wappler |
| 2,031,682 | A | 2/1936 | Wappler et al. |
| 2,176,479 | A | 10/1939 | Willis |
| 2,305,156 | A | 12/1942 | Grubel |
| 2,632,661 | A | 3/1953 | Cristofv |
| 2,668,538 | A | 2/1954 | Baker |
| 2,796,065 | A | 6/1957 | Kapp |
| 3,459,187 | A | 8/1969 | Pallotta |
| 3,643,663 | A | 2/1972 | Sutter |
| 3,651,811 | A | 3/1972 | Hildebrandt et al. |
| 3,862,630 | A | 1/1975 | Balamuth |
| 3,866,610 | A | 2/1975 | Kletschka |
| 3,911,766 | A | 10/1975 | Fridolph et al. |
| 3,920,021 | A | 11/1975 | Hiltebrandt |
| 3,921,641 | A | 11/1975 | Hulka |
| 3,938,527 | A | 2/1976 | Rioux et al. |
| 3,952,749 | A | 4/1976 | Fridolph et al. |
| 4,005,714 | A | 2/1977 | Hiltebrandt |
| 4,041,952 | A | 8/1977 | Morrison, Jr. et al. |

(Continued)

FOREIGN PATENT DOCUMENTS

CA    2104423    2/1994

(Continued)

OTHER PUBLICATIONS

Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.

(Continued)

*Primary Examiner*—Roy D. Gibson
*Assistant Examiner*—Aaron Roane

(57) ABSTRACT

An over shoe for use with electrosurgical instruments having a pair of juxtaposed jaw members pivotably associated with one another, at least one of which includes an electrically conductive surface disposed thereon which is in electrical engagement with an electrosurgical energy source. According to one aspect of the present disclosure, the over shoe includes a tissue contacting wall configured and dimensioned to selectively and substantially overlie the electrically conductive surface of the electrosurgical instrument. The tissue contacting wall is fabricated from a non-conductive material and includes a plurality of apertures formed therethrough. In another embodiment, the tissue contacting wall is electrically conductive and is configured for selective engagement atop on of the jaw members.

25 Claims, 14 Drawing Sheets

U.S. PATENT DOCUMENTS

| | | |
|---|---|---|
| 4,074,718 A | 2/1978 | Morrison, Jr. |
| 4,088,134 A | 5/1978 | Mazzariello |
| 4,127,222 A * | 11/1978 | Adams ..................... 223/101 |
| 4,128,099 A | 12/1978 | Bauer |
| 4,165,746 A | 8/1979 | Burgin |
| 4,300,564 A | 11/1981 | Furihata |
| 4,370,980 A | 2/1983 | Lottick |
| 4,416,276 A | 11/1983 | Newton et al. |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| D295,893 S | 5/1988 | Sharkany et al. |
| D295,894 S | 5/1988 | Sharkany et al. |
| 4,763,669 A | 8/1988 | Jaeger |
| 4,827,929 A | 5/1989 | Hodge |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,084,057 A | 1/1992 | Green et al. |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Xamiyama et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,318,589 A | 6/1994 | Lichtman |
| 5,324,289 A | 6/1994 | Eggers |
| 5,330,471 A | 7/1994 | Eggers |
| 5,334,183 A | 8/1994 | Wuchinich |
| 5,334,215 A | 8/1994 | Chen |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,423,810 A | 6/1995 | Goble et al. |
| 5,425,739 A | 6/1995 | Jessen |
| 5,429,616 A | 7/1995 | Schaffer |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,542,945 A | 8/1996 | Fritzsch |
| 5,558,672 A | 9/1996 | Edwards et al. |
| 5,562,699 A | 10/1996 | Heimberger et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,582,611 A | 12/1996 | Tsukagoshi et al. |
| 5,585,896 A | 12/1996 | Yamazaki et al. |
| 5,590,570 A | 1/1997 | LeMaire, III et al. |
| 5,601,601 A | 2/1997 | Tal et al. |
| 5,603,711 A | 2/1997 | Parins et al. |
| 5,603,723 A | 2/1997 | Aranyi et al. |
| 5,611,798 A | 3/1997 | Eggers |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,658,281 A | 8/1997 | Heard |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,681,282 A | 10/1997 | Eggers et al. |
| 5,693,051 A | 12/1997 | Schulze et al. |
| 5,695,522 A | 12/1997 | LeMaire, III et al. |
| 5,700,261 A | 12/1997 | Brinkerhoff |
| 5,702,390 A | 12/1997 | Austin et al. |
| 5,707,369 A | 1/1998 | Vaitekunas et al. |

| | | | | | |
|---|---|---|---|---|---|
| 5,709,680 A | 1/1998 | Yates et al. | 6,096,031 A | 8/2000 | Mitchell et al. |
| 5,716,366 A | 2/1998 | Yates | 6,096,037 A | 8/2000 | Mulier et al. |
| 5,727,428 A | 3/1998 | LeMaire, III et al. | 6,099,539 A | 8/2000 | Howell et al. |
| 5,735,848 A | 4/1998 | Yates et al. | 6,099,550 A | 8/2000 | Yoon |
| 5,743,906 A | 4/1998 | Parins et al. | 6,102,909 A | 8/2000 | Chen et al. |
| 5,755,717 A | 5/1998 | Yates et al. | 6,110,171 A | 8/2000 | Rydell |
| 5,766,130 A | 6/1998 | Selmonosky | 6,113,596 A | 9/2000 | Hooven et al. |
| 5,766,166 A | 6/1998 | Hooven | 6,113,598 A | 9/2000 | Baker |
| 5,766,170 A | 6/1998 | Eggers | 6,117,158 A | 9/2000 | Measamer et al. |
| 5,769,849 A | 6/1998 | Eggers | 6,123,701 A | 9/2000 | Nezhat |
| 5,772,655 A | 6/1998 | Bauer et al. | H1904 H | 10/2000 | Yates et al. |
| 5,772,670 A | 6/1998 | Brosa | 6,126,658 A | 10/2000 | Baker |
| 5,776,128 A | 7/1998 | Eggers | 6,152,923 A | 11/2000 | Ryan |
| 5,776,130 A | 7/1998 | Buysse et al. | 6,174,309 B1 | 1/2001 | Wrublewski et al. |
| 5,779,701 A | 7/1998 | McBrayer et al. | 6,179,834 B1 | 1/2001 | Buysse et al. |
| 5,792,137 A | 8/1998 | Carr et al. | 6,179,837 B1 | 1/2001 | Hooven |
| 5,792,177 A | 8/1998 | Kaseda | 6,183,467 B1 | 2/2001 | Shapeton et al. |
| 5,797,938 A | 8/1998 | Paraschac et al. | 6,187,003 B1 | 2/2001 | Buysse et al. |
| 5,797,958 A | 8/1998 | Yoon | 6,190,386 B1 | 2/2001 | Rydell |
| 5,800,449 A | 9/1998 | Wales | 6,193,718 B1 | 2/2001 | Kortenbach et al. |
| 5,807,393 A | 9/1998 | Williamson, IV et al. | 6,206,876 B1 | 3/2001 | Levine et al. |
| 5,810,808 A | 9/1998 | Eggers | 6,206,877 B1 | 3/2001 | Kese et al. |
| 5,810,811 A | 9/1998 | Yates et al. | 6,206,896 B1 | 3/2001 | Howell et al. |
| 5,810,877 A | 9/1998 | Roth et al. | 6,217,602 B1 | 4/2001 | Redmon |
| 5,814,043 A | 9/1998 | Shapeton | 6,224,593 B1 | 5/2001 | Ryan et al. |
| 5,820,630 A | 10/1998 | Lind | 6,228,080 B1 | 5/2001 | Gines |
| 5,827,271 A | 10/1998 | Buysse et al. | 6,228,083 B1 | 5/2001 | Lands et al. |
| 5,827,279 A | 10/1998 | Hughett et al. | 6,267,761 B1 | 7/2001 | Ryan |
| 5,827,281 A | 10/1998 | Levin | 6,270,497 B1 | 8/2001 | Sekino et al. |
| 5,833,690 A | 11/1998 | Yates et al. | 6,270,508 B1 | 8/2001 | Klieman et al. |
| 5,843,080 A | 12/1998 | Fleenor et al. | 6,273,887 B1 | 8/2001 | Yamauchi et al. |
| 5,849,022 A | 12/1998 | Sakashita et al. | 6,273,902 B1 | 8/2001 | Fogarty et al. |
| 5,853,412 A | 12/1998 | Mayenberger | 6,277,117 B1 * | 8/2001 | Tetzlaff et al. ................ 606/48 |
| 5,860,976 A | 1/1999 | Billings et al. | 6,280,458 B1 | 8/2001 | Boche et al. |
| 5,876,401 A | 3/1999 | Schulze et al. | 6,283,961 B1 | 9/2001 | Underwood et al. |
| 5,891,141 A | 4/1999 | Rydell | D449,886 S | 10/2001 | Tetzlaff et al. |
| 5,891,142 A | 4/1999 | Eggers et al. | 6,322,561 B1 | 11/2001 | Eggers et al. |
| 5,893,863 A | 4/1999 | Yoon | 6,334,860 B1 | 1/2002 | Dorn |
| 5,893,875 A | 4/1999 | O'Connor et al. | 6,334,861 B1 | 1/2002 | Chandler et al. |
| 5,893,877 A | 4/1999 | Gampp, Jr. et al. | 6,350,264 B1 | 2/2002 | Hooven |
| 5,902,301 A | 5/1999 | Olig | 6,352,536 B1 | 3/2002 | Buysse et al. |
| 5,906,630 A | 5/1999 | Anderhub et al. | D457,958 S | 5/2002 | Dycus et al. |
| 5,908,420 A | 6/1999 | Parins et al. | D457,959 S | 5/2002 | Tetzlaff et al. |
| 5,911,719 A | 6/1999 | Eggers | 6,387,094 B1 | 5/2002 | Eitenmuller |
| 5,913,874 A | 6/1999 | Berns et al. | 6,387,106 B1 | 5/2002 | Howell et al. |
| 5,921,984 A | 7/1999 | Sutcu et al. | 6,387,112 B1 | 5/2002 | Fogarty et al. |
| 5,925,043 A | 7/1999 | Kumar et al. | 6,398,779 B1 | 6/2002 | Buysse et al. |
| 5,935,126 A | 8/1999 | Riza | 6,402,747 B1 | 6/2002 | Lindemann et al. |
| 5,944,718 A | 8/1999 | Dafforn et al. | 6,409,728 B1 | 6/2002 | Ehr et al. |
| 5,951,549 A | 9/1999 | Richardson et al. | H2037 H | 7/2002 | Yates et al. |
| 5,954,720 A | 9/1999 | Wilson et al. | 6,419,675 B1 | 7/2002 | Gallo, Sr. |
| 5,957,923 A | 9/1999 | Hahnen et al. | 6,425,896 B1 | 7/2002 | Baltschun et al. |
| 5,961,514 A | 10/1999 | Long et al. | 6,443,952 B1 | 9/2002 | Mulier et al. |
| 5,976,132 A | 11/1999 | Morris | 6,443,970 B1 | 9/2002 | Schulze et al. |
| 5,984,939 A | 11/1999 | Yoon | 6,451,018 B1 | 9/2002 | Lands et al. |
| 5,989,277 A | 11/1999 | LeMaire, III et al. | 6,458,128 B1 | 10/2002 | Schulze |
| 6,004,335 A | 12/1999 | Vaitekunas et al. | 6,458,130 B1 | 10/2002 | Frazier et al. |
| 6,010,516 A | 1/2000 | Hulka et al. | 6,464,701 B1 | 10/2002 | Hooven et al. |
| 6,024,741 A | 2/2000 | Williamson et al. | 6,464,704 B2 | 10/2002 | Schmaltz et al. |
| 6,024,744 A | 2/2000 | Kese et al. | 6,503,248 B1 | 1/2003 | Levine |
| 6,033,399 A | 3/2000 | Gines | 6,506,189 B1 | 1/2003 | Rittman, III et al. |
| 6,039,733 A | 3/2000 | Buysse et al. | 6,511,480 B1 | 1/2003 | Tetzlaff et al. |
| 6,041,679 A | 3/2000 | Slater et al. | 6,514,251 B1 | 2/2003 | Ni et al. |
| 6,050,996 A | 4/2000 | Schmaltz et al. | 6,544,264 B2 | 4/2003 | Levine et al. |
| 6,053,914 A | 4/2000 | Eggers et al. | 6,569,162 B2 | 5/2003 | He |
| 6,053,933 A | 4/2000 | Balazs et al. | 6,620,161 B2 | 9/2003 | Schulze et al. |
| D424,694 S | 5/2000 | Tetzlaff et al. | 6,652,521 B2 | 11/2003 | Schulze |
| D425,201 S | 5/2000 | Tetzlaff et al. | 6,656,177 B2 | 12/2003 | Truckai et al. |
| 6,059,782 A | 5/2000 | Novak et al. | 6,669,696 B2 | 12/2003 | Bacher et al. |
| RE36,795 E | 7/2000 | Rydell | 6,685,724 B1 | 2/2004 | Haluck |
| 6,083,223 A | 7/2000 | Baker | 6,726,068 B2 * | 4/2004 | Miller ........................ 223/101 |
| 6,086,586 A | 7/2000 | Hooven | 6,733,498 B2 | 5/2004 | Paton et al. |
| 6,090,107 A | 7/2000 | Borgmeier et al. | 6,743,229 B2 | 6/2004 | Buysse et al. |

| | | |
|---|---|---|
| 6,770,072 B1 | 8/2004 | Truckai et al. |
| 6,773,434 B2 | 8/2004 | Ciarrocca |
| 6,776,780 B2 | 8/2004 | Mulier et al. |
| D496,997 S | 10/2004 | Dycus et al. |
| 6,802,843 B2 | 10/2004 | Truckai et al. |
| D499,181 S | 11/2004 | Dycus et al. |
| 6,818,000 B2 | 11/2004 | Muller et al. |
| 6,928,716 B2 | 8/2005 | Baker et al. |
| 6,929,644 B2 | 8/2005 | Truckai et al. |
| 6,932,810 B2 | 8/2005 | Ryan |
| 6,942,662 B2 | 9/2005 | Goble et al. |
| 6,964,662 B2 | 11/2005 | Kidooka |
| 7,033,354 B2 | 4/2006 | Keppel |
| 7,083,618 B2 | 8/2006 | Couture et al. |
| 7,090,673 B2 | 8/2006 | Dycus et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,118,570 B2 | 10/2006 | Tetzlaff et al. |
| 7,118,587 B2 | 10/2006 | Dycus et al. |
| 2002/0013583 A1 | 1/2002 | Camran et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0018331 A1 | 1/2003 | Dycus et al. |
| 2003/0069571 A1 | 4/2003 | Treat et al. |
| 2003/0078578 A1 | 4/2003 | Truckai et al. |
| 2003/0139741 A1 | 7/2003 | Goble et al. |
| 2003/0139742 A1 | 7/2003 | Wampler et al. |
| 2003/0158549 A1 | 8/2003 | Swanson |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0236325 A1 | 12/2003 | Bonora |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0116979 A1 | 6/2004 | Truckai et al. |
| 2004/0147925 A1 | 7/2004 | Buysse et al. |
| 2004/0225288 A1 | 11/2004 | Buysse et al. |
| 2004/0230189 A1 | 11/2004 | Keppel |
| 2004/0236325 A1 | 11/2004 | Tetzlaff et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2005/0004564 A1 | 1/2005 | Wham et al. |
| 2005/0004568 A1 | 1/2005 | Lawes et al |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0107785 A1 | 5/2005 | Dycus et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0119655 A1 | 6/2005 | Moses et al. |
| 2005/0149151 A1 | 7/2005 | Orszulak et al. |
| 2006/0064085 A1 | 3/2006 | Schechter et al. |
| 2006/0079891 A1 | 4/2006 | Arts et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |

FOREIGN PATENT DOCUMENTS

| | | |
|---|---|---|
| DE | 2415263 | 10/1975 |
| DE | 8712328 | 3/1988 |
| DE | 29616210 | 1/1997 |
| DE | 19608716 | 4/1997 |
| DE | 19751108 | 5/1999 |
| EP | 0364216 A1 | 4/1990 |
| EP | 518230 A1 | 12/1992 |
| EP | 0 541 930 B1 | 5/1993 |
| EP | 0572131 | 12/1993 |
| EP | 584787 A1 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 853922 A1 | 7/1998 |
| EP | 0875209 A1 | 11/1998 |
| EP | 0878169 A1 | 11/1998 |
| EP | 0887046 A3 | 1/1999 |
| EP | 0923907 A1 | 6/1999 |
| EP | 0986990 A1 | 3/2000 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1330991 A1 | 7/2003 |
| EP | 1486177 A2 | 6/2004 |
| EP | 1532932 A1 | 5/2005 |
| GB | WO89/00757 * | 1/1989 |
| GB | 2214430 A | 6/1989 |
| JP | 501068 | 9/1984 |
| JP | 502328 | 3/1992 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| SU | 401367 | 11/1974 |
| WO | WO 92/06642 | 4/1992 |
| WO | WO 94/08524 A | 4/1994 |
| WO | WO 95/02369 | 1/1995 |
| WO | WO 95/07662 | 3/1995 |
| WO | WO 96/022056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |

| | | |
|---|---|---|
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 A | 3/1999 |
| WO | WO 99/40857 | 8/1999 |
| WO | WO 99/040861 | 8/1999 |
| WO | WO 99/51158 | 10/1999 |
| WO | WO 99/066850 | 12/1999 |
| WO | WO 99/66850 A | 12/1999 |
| WO | WO 00/24330 | 5/2000 |
| WO | WO 00/24331 | 5/2000 |
| WO | WO 00/41638 | 7/2000 |
| WO | WO 00/53112 | 9/2000 |
| WO | WO 01/17448 A | 3/2001 |
| WO | WO 01/54604 | 8/2001 |
| WO | WO 02/07627 | 1/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080796 A1 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/101311 | 12/2003 |
| WO | WO 04/032777 | 4/2004 |
| WO | WO 2004/052221 A1 | 6/2004 |
| WO | WO 04/073490 | 9/2004 |
| WO | WO 2004/082495 | 9/2004 |
| WO | WO 2004/082495 A1 | 9/2004 |
| WO | WO 2004/098383 A1 | 11/2004 |
| WO | WO 04/103156 | 12/2004 |

OTHER PUBLICATIONS

Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics FIGO World Congress 2000, Washington, D.C.
Crawford et al. "Use of the LigaSure Vessel Sealing System in Urologic Cancer Surger" Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.

Chung et al., "Clinical Experience of Sutureless Closed Hemorrhoidectomy with LigaSure" Diseases of the Colon & Rectum vol. 46, No. 1 Jan 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, ☐Apr. 2001 pp. 236-237.
Michael Choti, "Abdominoperineal Resection with the LigaSure Vessel Sealing System and LigaSure Atlas 20 cm Open Instrument" Innovations That Work, ☐Jun. 2003.
Craig Johnson, "Use of the LigaSure Vessel Sealing System in Bloodless Hemorrhoidectomy" Innovations That Work, ☐Mar. 2000.
Muller et al., "Extended Left Hemicolectomy Using the LigaSure Vessel Sealing System" Innovations That Work,☐Sep. 1999.
Herman et al., "Laparoscopic Intestinal Resection With the LigaSure Vessel Sealing System: A Case Report" Innovations That Work,☐Feb. 2002.
Carus et al., "Initial Experience With The LigaSure Vessel Sealing System in Abdominal Surgery" Innovations That Work,☐Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
Sengupta et al., "Use of a Computer-Controlled Bipolar Diathermy System in Radical Prostatectomies and Other Open Urological Surgery" ANZ Journal of Surgery (2001) 71.9 pp. 538-540.
Joseph Ortenberg "LigaSure System Used in Laparoscopic 1st and 2nd Stage Orchiopexy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.
"Innovations In Electrosurgery" Sales/Product Literature; Dec. 31, 2000.
LigaSure Vessel Sealing System, the Seal of Confidence in General, Gynecologic, Urologic, and Laparoscopic Surgery Sales/Product Literature; Jan. 2004.
Olsson et al. "Radical Cystectomy in Females" Current Surgical Techniques in Urology, vol. 14, Issue 3, 2001.
Dulemba et al. "Use of a Bipolar Electrothermal Vessel Sealer in Laparoscopically Assisted Vaginal Hysterectomy" Sales Product Literature; Jan. 2004.
Johnson et al. "Evaluation of a Bipolar electrothermal Vessel Sealing Device in Hemorrhoidectomy" Sales Product Literature; Jan. 2004.
International Search Report PCT/US01/11224 dated Nov. 13, 2001.
International Search Report EP 98958575.7 dated Sep. 20, 2002.
International Search Report EP 04013772 dated Apr. 1, 2005.
International Search Report EP 05013895 dated Oct. 14, 2005.
International Search Report EP 05017281 dated Nov. 16, 2005.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
US 6,090,109, 07/2000, Lands et al. (withdrawn)
US 6,663,629, 12/2003, Buysse et al. (withdrawn)

* cited by examiner

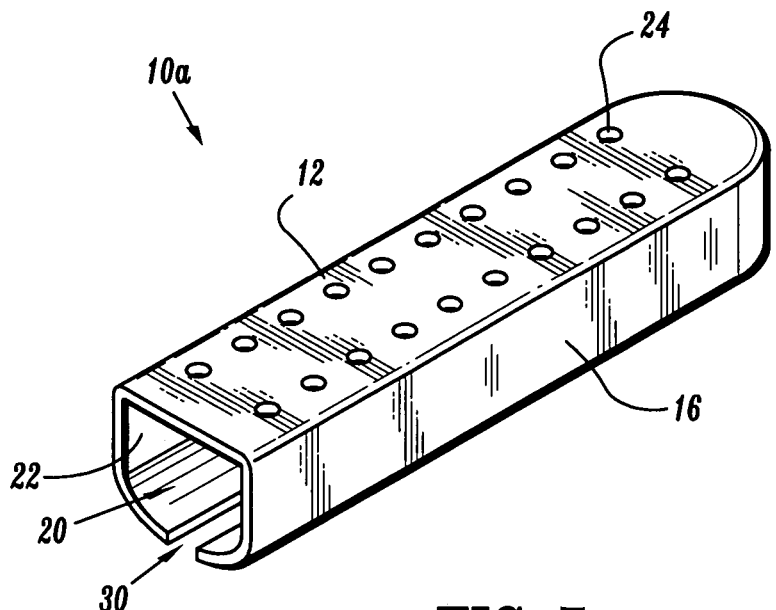
FIG. 5
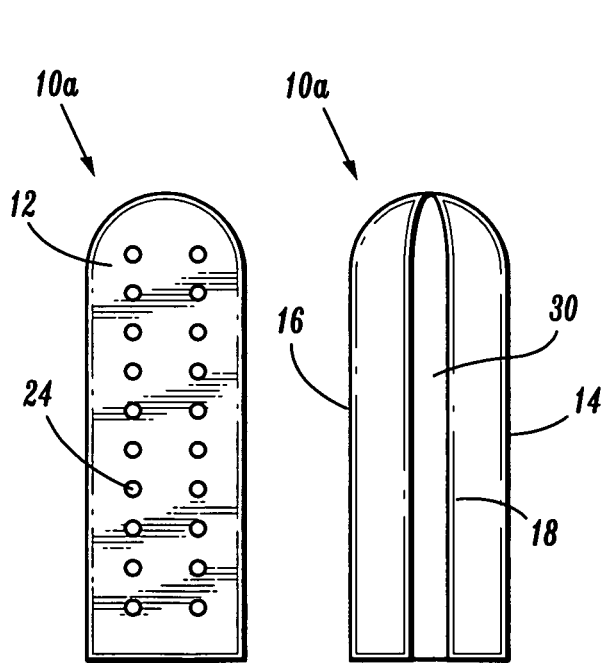
FIG. 6   FIG. 7
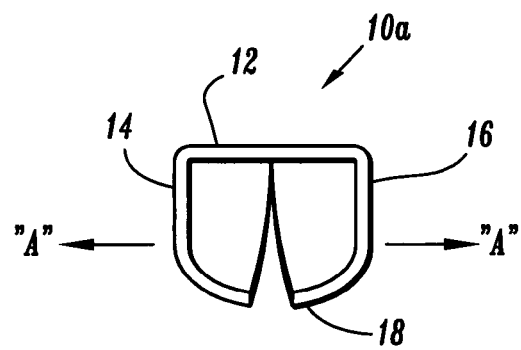
FIG. 8
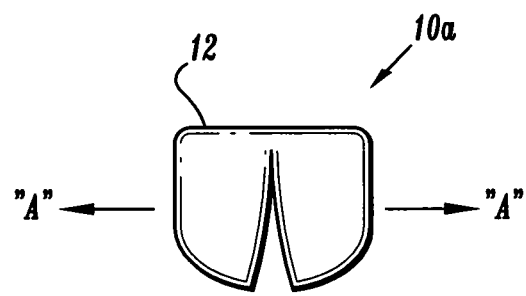
FIG. 9

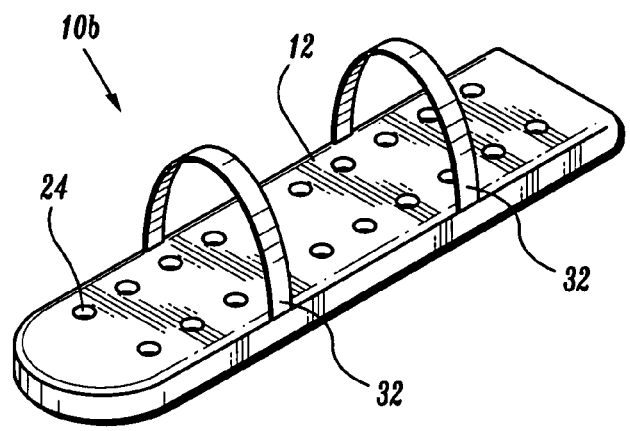
FIG. 10
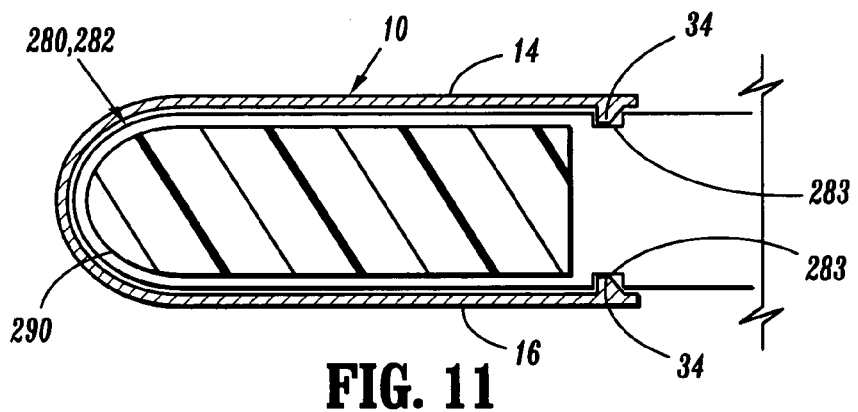
FIG. 11
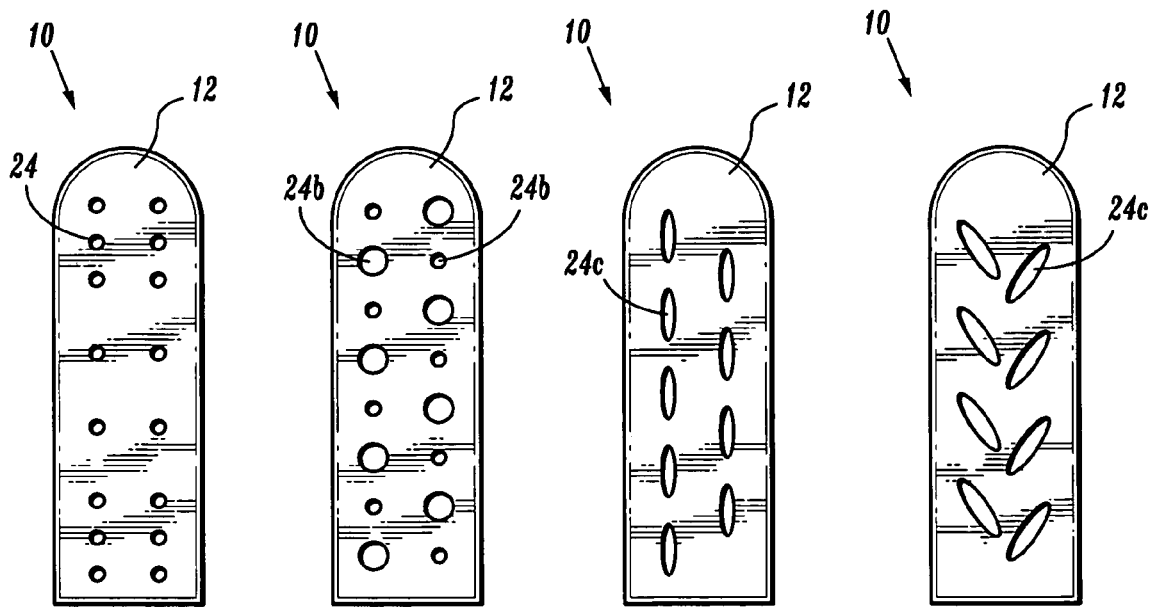
FIG. 12  FIG. 13  FIG. 14  FIG. 15

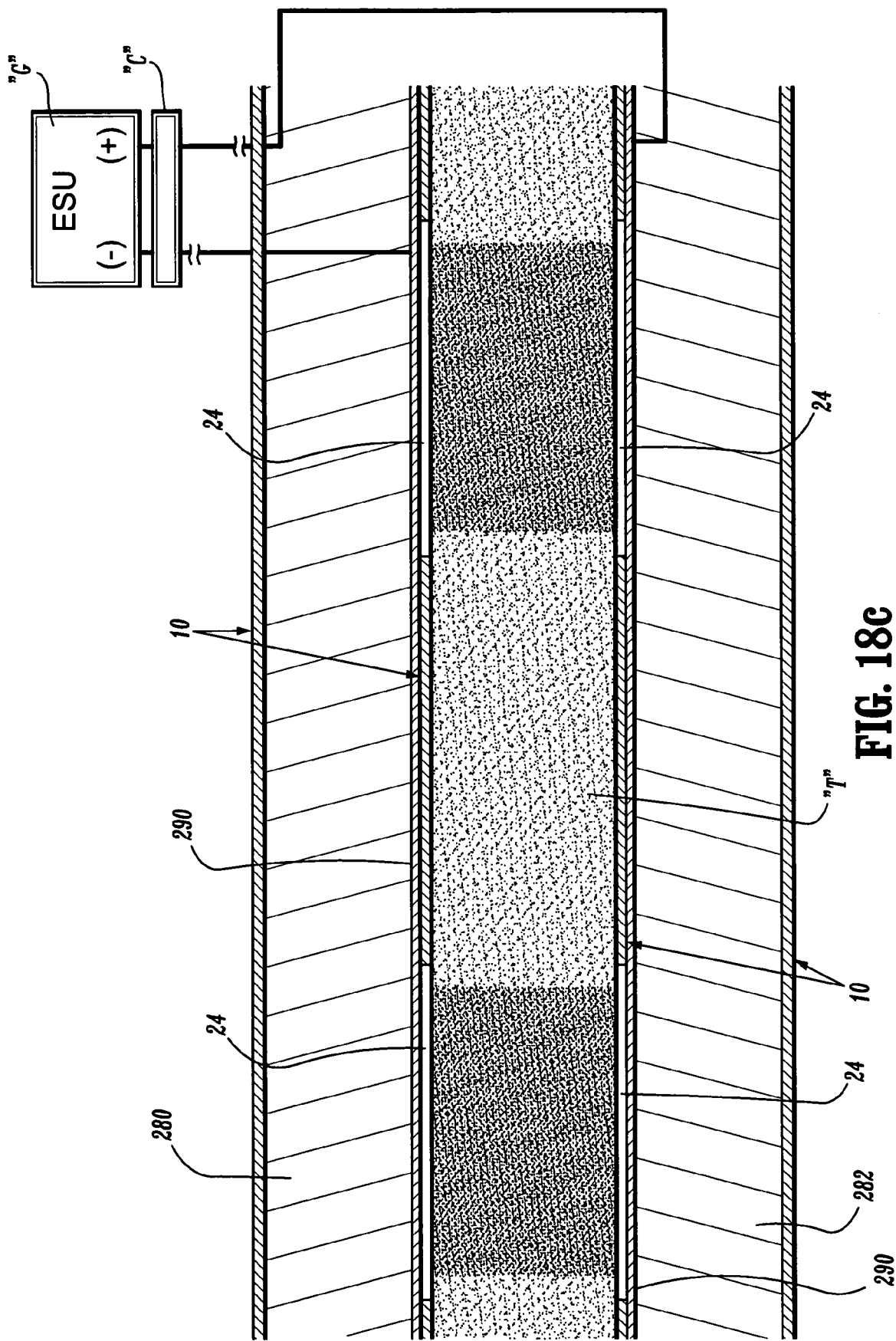

ELECTRICALLY CONDUCTIVE/INSULATIVE OVER-SHOE FOR TISSUE FUSION

BACKGROUND

1. Technical Field

The present disclosure relates to electrosurgical instruments and, more particularly, an over-shoe for use in cooperation with electrosurgical instruments for controlling the amount of electrosurgical energy delivered to the tissue.

2. Description of Related Art

A hemostat and/or forceps is a simple plier-like tool which uses mechanical action between its jaws to constrict vessels and is commonly used in open surgical procedures to grasp, dissect and/or clamp tissue. Electrosurgical hemostats and/or forceps utilize both mechanical clamping action and electrical energy to effect hemostasis by heating the tissue and blood vessels, between its jaws, to cut, blend and/or coagulate tissue. An electrode operatively associated with each opposing jaw member is charged to a different electric potential such that when the jaw members grasp tissue therebetween, electrical energy can be selectively transferred through the tissue. A surgeon can cut, blend, coagulate/desiccate and/or simply reduce or slow bleeding, by controlling the intensity, frequency and duration of the electrosurgical energy applied between the electrodes and through the tissue.

"Tissue heating" is generally proportional to the square of the amount of current being generated through tissue while "tissue vaporization" is generally proportional to current and is generally proportional to the amount of energy in an arc. The amount of energy in the arc, in combination with the "Cathode Fall Voltage", derives the "power for vaporization". "Thermal spread" is dependent on the amount of heat generated within the tissue and is dependent on tissue resistivity and the arc energy squared. As can be appreciated, the control of "thermal spread" is an important factor in determining and controlling the depth of tissue treatment.

Accordingly, during electrosurgery, an increase or decrease in the amount of current provides and/or creates a different effect on the tissue. This phenomenon is due to a variable referred to as the crest factor (CF). The crest factor can be calculated using the formula: $CF=V_{PEAK}/V_{RMS}$, where $V_{PEAK}$ is the positive peak of the waveform and $V_{RMS}$ is the "Root Mean Square" or RMS value of the waveform. The crest factor can also be calculated using the formula: $CF=[(1-D)/D]^{1/2}$, where D is the duty cycle of the waveform and is defined as $D=T_1/(T_1+T_2)$.

An increase in the crest factor results in more current per arc at a given power setting. Further, since "tissue heating" is proportional to the current through the tissue squared, and "tissue vaporization" is proportional to the amount of current being generated through the tissue, a doubling of current per arc results in four times as much tissue heating and twice the amount of tissue vaporization when an electrode of an electrosurgical hemostat and/or forceps, connected to the electrosurgical generator system, contacts the tissue.

Based on the above formulas, it is evident that when operating an electrosurgical generator system in either the "cut", "blend", "coagulate" or seal mode, the range of the crest factor varies from one mode to another. For the purposes herein, "coagulation" is defined as a process of desiccating tissue wherein the tissue cells are ruptured and dried. "Vessel sealing" is defined as the process of liquefying the collagen in the tissue so that it reforms into a fused mass with significantly-reduced demarcation between the opposing tissue structures (opposing walls of the lumen). Coagulation of small vessels is usually sufficient to permanently close them. Larger vessels need to be sealed to assure permanent closure.

Commonly assigned U.S. Application Serial Nos. PCT Application Serial No. PCT/US01/11340; U.S. application Ser. No. 10/116,824; and PCT Application Serial No. PCT/US01/11420 (all of which are hereby incorporated by reference herein) teach that to effectively seal tissue or vessels, especially large vessels, two predominant mechanical parameters must be accurately controlled: 1) the pressure applied to the vessel; and 2) the gap distance between the conductive tissue contacting surfaces (electrodes). As can be appreciated, both of these parameters are affected by the thickness of the vessel or tissue being sealed. Accurate application of pressure is important for several reasons: 1) to oppose the walls of the vessel; 2) to reduce the tissue impedance to a low enough value that allows enough electrosurgical energy through the tissue; 3) to overcome the forces of expansion during tissue heating; and 4) to contribute to the end tissue thickness which is an indication of a good seal. It has been determined that a typical sealed vessel wall is optimum between about 0.001 inches and about 0.006 inches.

With respect to electrosurgically treating relatively smaller vessels, for effective sealing, the pressure applied to the vessel becomes less relevant and the gap distance between the electrically conductive surfaces of the electrodes becomes more significant. In other words, the chances of the two electrodes touching one another during activation increases as the tissue thickness and the vessels become smaller.

As can be appreciated, when cutting, blending or coagulating vessels, the tissue disposed between the two opposing jaw members is essentially destroyed. Other known electrosurgical instruments include blade members or shearing members which simply cut tissue in a mechanical and/or electromechanical manner and, as such, also destroy tissue viability. With respect to electrosurgically treating relatively larger vessels and/or soft tissues (e.g., lung, intestine, lymph ducts, etc.), to promote healing, the above-identified surgical treatments are generally impractical due to the fact that in each instance the tissue or a significant portion thereof is essentially destroyed to create the desired surgical effect (e.g., cutting, blending and/or cauterizing) which does not promote healing.

Accordingly, the need exists for electrosurgical accessories and/or devices (e.g., an electrically conductive or insulative over-shoe) which can be used in cooperation with existing electrosurgical instruments (e.g., electrosurgical forceps) for controlling and/or limiting the current (or current per arc on a micro level) and for controlling the degree of tissue heating and the degree of tissue vaporization.

In addition, the need exists for electrosurgical accessories and/or devices (e.g., an electrically conductive or insulative over-shoe) for cooperative use with existing electrosurgical instruments (e.g., electrosurgical forceps) which allow for the effective treatment of tissue and the effective maintenance of tissue viability across the treatment area to promote tissue healing.

SUMMARY

The present disclosure relates to an over shoe for use with electrosurgical instruments having a pair of juxtaposed jaw members pivotably associated with one another. At least one of the jaw members includes an electrically conductive surface disposed thereon and in electrical engagement with an electrosurgical energy source is disclosed. According to one aspect of the present disclosure, the over shoe includes a tissue contacting wall configured and dimensioned to selectively and substantially overlie (or be selectively positioned atop) the electrically conductive surface of the electrosurgical instrument. The tissue contacting wall is preferably fabricated from a non-conductive material and includes a plurality of apertures formed therethrough.

In one embodiment the over shoe includes a tissue contacting wall fabricated from a ceramic material. The tissue contacting wall desirably includes a plurality of apertures arranged in pairs along a length of the electrically conductive surface. It is envisioned that the apertures are randomly arranged.

It is contemplated that the apertures are evenly sized. It is further envisioned that the apertures are generally circular. In one embodiment, the apertures can have diameters of about 0.000394 inches (10 μm) to about 0.0394 inches (1000 μm). In another embodiment, the apertures may be much larger and being the range of about 0.001 inches (0.0254 millimeters) to about 0.15 inches (3.81 millimeters).

It is further contemplated that the apertures are elongated slots. The elongated slots can be in at least one of a parallel orientation with respect to the longitudinal axis and at an angle with respect to the longitudinal axis.

It is envisioned that the over shoe can further include a pair of side walls extending from lateral side edges of the tissue contacting wall, and a bottom wall interconnecting the pair of side walls, the tissue contacting wall, the bottom wall and the side walls defining a cavity configured and dimensioned to substantially receive a jaw member of the electrosurgical instrument. The bottom wall can include a longitudinally oriented slot running along a length thereof which promotes friction fit engagement between the over shoe and the jaw member.

The over shoe can include at least one band extending between and engaged with each side terminal edge of the tissue contacting wall. The over shoe can include at least one inter-engaging member extending from an inner surface of at least one of the pair of side walls, the at least one inter-engaging member being configured and dimensioned to engage a complementary recess formed in the jaw member. The at least one inter-engaging member registers the apertures of an over shoe placed on one of the pair of jaw members relative to the apertures of an over shoe placed on the other of the other of the pair of jaw members. It is contemplated that the apertures can be in vertical registration and/or offset.

The tissue contacting wall can have a thickness which is in the range of about 0.000394 inches (10 μm) to about 0.0394 inches (1000 μm). The thickness of the tissue contacting wall is non-uniform.

According to another aspect of the present disclosure, the over shoe can include a tissue contacting wall fabricated from a non-conductive material, the tissue contacting wall being configured and dimensioned to over lie an electrically conductive surface disposed on the electrosurgical instrument, the tissue contacting wall including at least one aperture extending therethrough. The tissue contacting wall is desirably fabricated from a ceramic material.

It is envisioned that the tissue contacting wall is fabricated from materials having a high Comparative Tracking Index, preferably the range of about 300 to about 600 volts.

It is further envisioned that the tissue contacting wall is fabricated from a group consisting of at least one of nylons, syndiotactic polystryrenes, polybutylene terephthalate, polycarbonate, acrylonitrile butadiene styrene, polyphthalamide, polymide, polyethylene terephthalate, polyamide-imide, acrylic, polystyrene, polyether sulfone, aliphatic polyketone, acetal copolymer, polyurethane, nylon with polyphenyleneoxide dispersion, and acrylonitrile styrene acrylate.

The present disclosure also relates to an over shoe for use with electrosurgical instruments which is capable of performing tissue sealing between two opposing jaw members, the over shoe including a tissue contacting wall fabricated from a conductive material which is disposed in electrical communication with a source of electrosurgical energy. The tissue contacting wall also includes at least one sidewall which depends therefrom which defines a slot for selectively receiving at least one jaw member. The tissue contacting wall also includes at least one aperture which extends therethrough. Preferably, the jaw member is made from an insulative material.

A second over shoe may be included which is designed to substantially overlie or sit atop the second jaw member such that the jaw members are capable of conducting bipolar energy therethrough.

The present disclosure also relates to an over shoe for use with electrosurgical instruments capable of performing tissue sealing between two opposing jaw members which includes a tissue contacting wall fabricated from a non-conductive material. The tissue contacting wall includes at least one sidewall which depends therefrom which defines a slot for selectively receiving at least one jaw member. The tissue contacting wall also includes at least one protrusion extending therefrom, the protrusion being disposed in electrical communication with a source of electrosurgical energy. For bipolar electrosurgical instruments, each jaw member may include an electrically conductive overshoe.

Further features of the above embodiments will become more readily apparent to those skilled in the art from the following detailed description of the apparatus taken in conjunction with the drawings.

BRIEF DESCRIPTION OF THE DRAWINGS

Various embodiments will be described herein below with reference to the drawings, wherein:

FIG. 5 is a rear perspective view of an over shoe in accordance with yet another embodiment of the present disclosure;

FIG. 6 is a top plan view of the over shoe of FIG. 5;

FIG. 7 is a bottom plan view of the over shoe of FIGS. 5 and 6;

FIG. 8 is a rear elevational view of the over shoe of FIGS. 5-7;

FIG. 9 is a front elevational view of the over shoe of FIGS. 5-8;

FIG. 10 is a bottom perspective view of an over shoe in accordance with still another embodiment of the present disclosure;

FIG. 11 is a top plan view of a jaw member of a forceps including an over shoe, with the tissue contacting wall thereof removed therefrom, mounted thereon and illustrating an exemplary positioning arrangement for engagement of the over shoe to the jaw member;

FIG. 12 is a top plan view of an over shoe illustrating an exemplary aperture pattern formed therein;

FIG. 13 is a top plan view of an over shoe illustrating another exemplary aperture pattern formed therein;

FIG. 14 is a top plan view of an over shoe illustrating still another exemplary aperture pattern formed therein;

FIG. 15 is a top plan view of an over shoe illustrating yet another exemplary hole pattern formed therein;

FIG. 18C is an enlarged schematic side elevational view showing the individual micro-seal sites and the viable tissue areas between the two jaw members after activation of the electrode assembly;

DETAILED DESCRIPTION

Figure 1A:
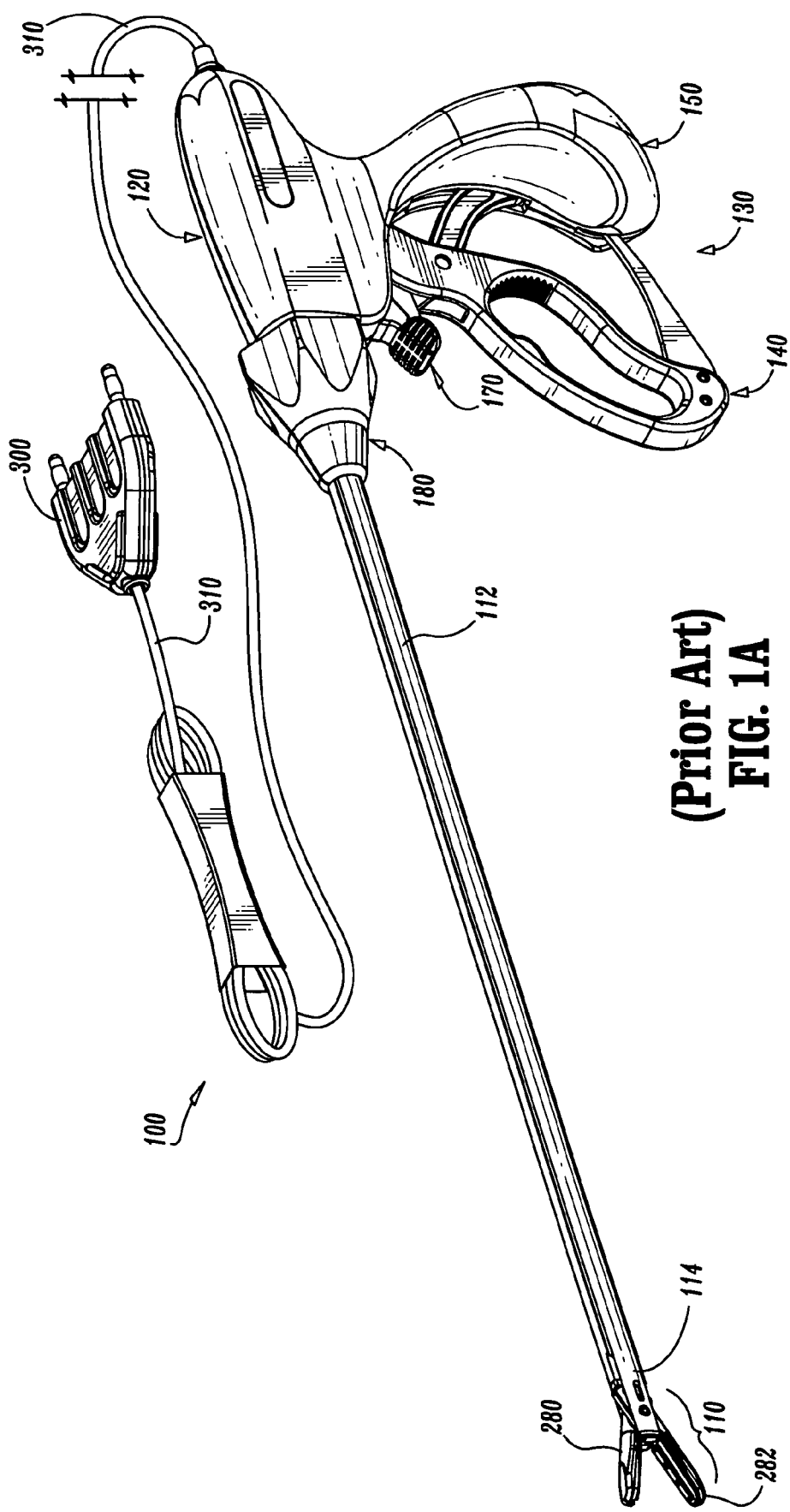
FIG. 1A is a perspective view of a prior art endoscopic forceps.

Preferred embodiments of the presently disclosed instruments, devices and accessories will now be described in detail with reference to the drawing figures wherein like reference numerals identify similar or identical elements. In the drawings and in the description which follows, the term "proximal", as is traditional, will refer to the end of the instrument, device and/or accessory which is furthest from the operator while the term "distal" will refer to the end of the instrument, device and/or accessory which is closest to the operator.

Figure 1B:
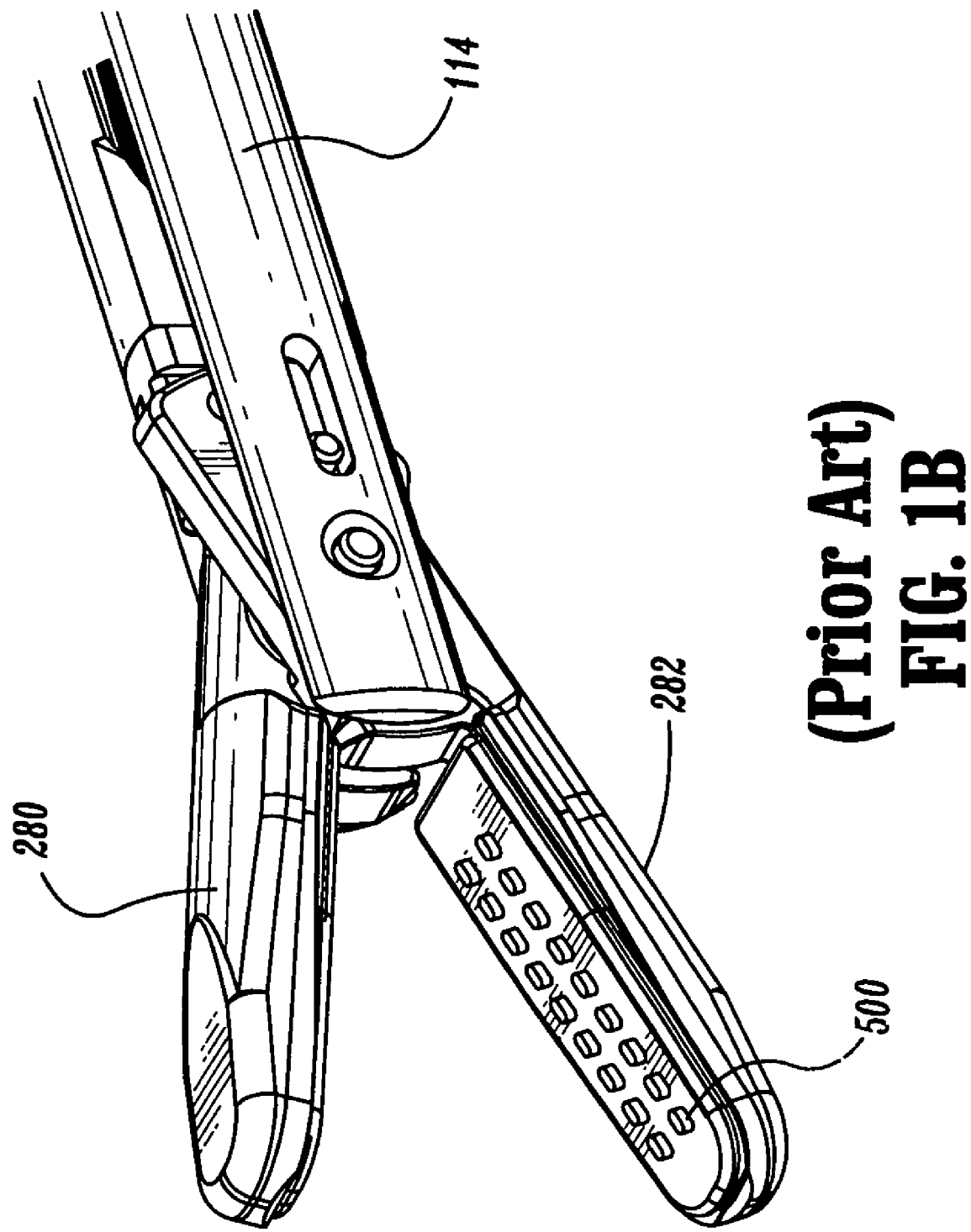
FIG. 1B is an enlarged perspective view of a jaw assembly of the prior art endoscopic forceps of FIG. 1A.

Referring to FIGS. 1A and 1B, a prior art bipolar forceps, for use in various endoscopic surgical procedures, is shown generally as 100. Forceps 100 generally includes a housing 120, a handle assembly 130, a rotating assembly 180, an activation assembly 170 and an electrode assembly 110 which mutually cooperate to grasp and seal tissue.

More particularly, forceps 100 includes a shaft 112 which has a distal end 114 dimensioned to mechanically engage a jaw assembly 110 and a proximal end 116 which mechanically engages housing 120. Shaft 112 may be bifurcated at the distal end 114 thereof to receive jaw assembly 110. Proximal end 116 of shaft 112 mechanically engages rotating assembly 180 to facilitate rotation of jaw assembly 110.

Forceps 100 also includes an electrical interface or plug 300 which connects forceps 100 to a source of electrosurgical energy, e.g., an electrosurgical generator (not shown). An electrical cable 310 extends from plug 300 and is securely connected to housing 120 of forceps 100. Cable 310 is internally divided within housing 120 to transmit electrosurgical energy through various electrical feed paths to jaw assembly 110. Handle assembly 130 includes a fixed handle 150 and a movable handle 140. Fixed handle 150 is integrally associated with housing 120 and handle 140 is movable relative to fixed handle 150 to actuate a pair of opposing jaw members 280 and 282 of jaw assembly 110.

Figure 2A:
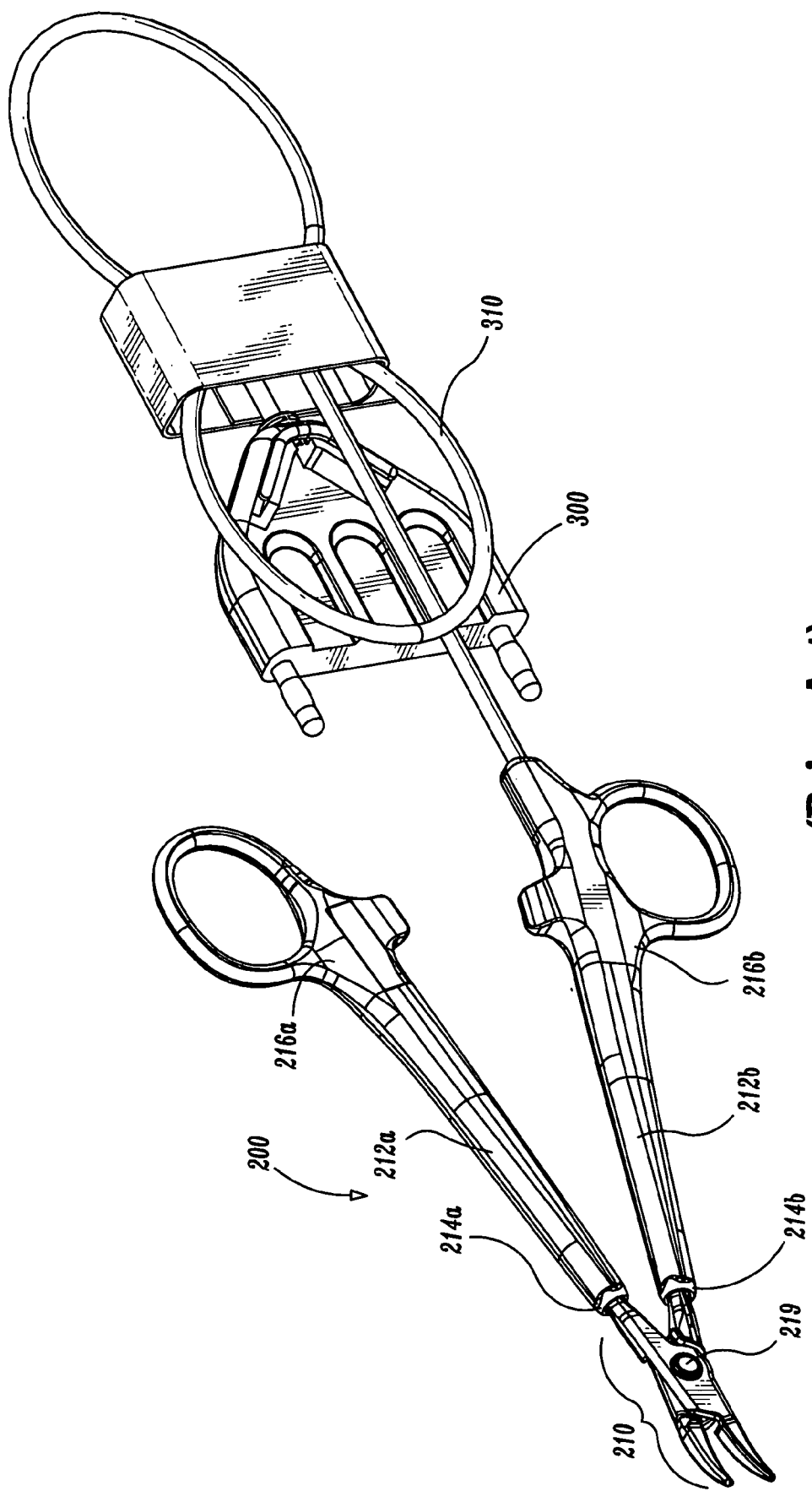
FIG. 2A is a perspective view of a prior art open forceps.
Figure 2B:
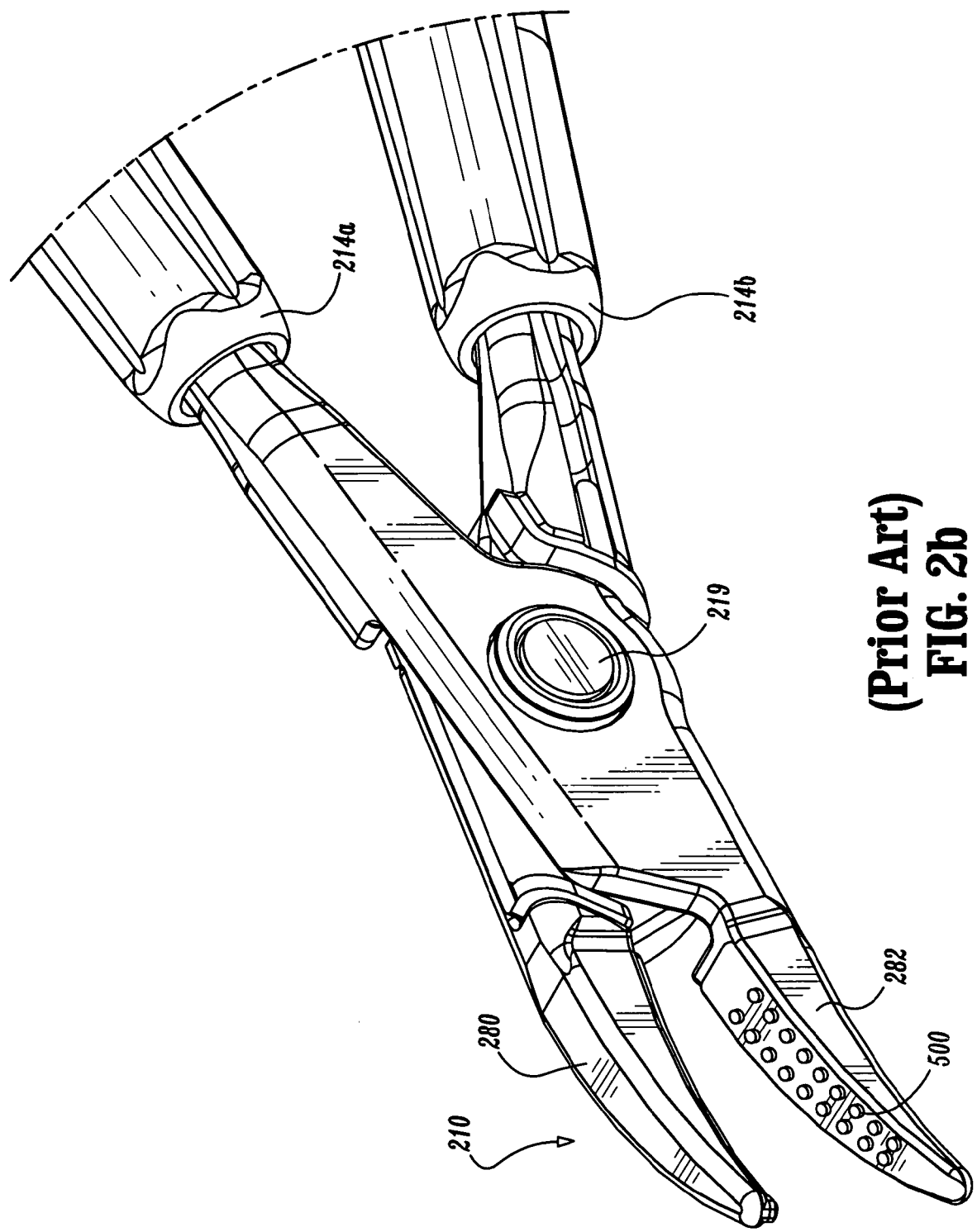
FIG. 2B is an enlarged perspective view of a jaw assembly of the prior art open forceps of FIG. 2A.

Referring now to FIGS. 2A and 2B, a prior art open forceps is generally shown as 200. Open forceps 200 is generally in the form of a pair of scissors and includes a pair of elongated shaft portions 212a, 212b each having a proximal end 216a, 216b, respectively, and a distal end 214a, 214b, respectively. Open forceps 200 includes a jaw assembly 210 which attaches to distal end 214a, 214b of shaft portions 212a, 212b, respectively. Jaw assembly 210 includes opposing jaw members 280, 282 which are pivotably connected about a pivot pin 219.

One of shafts 212a, 212b, is operatively connected to a source of electrosurgical energy, such as an electrosurgical generator (not shown), via an electrosurgical cable 310. A proximal end of cable 310 includes a similar plug 300 as described above.

As best seen in FIGS. 1B and 2B, various electrical connections of electrode assemblies 110, 210 (not shown) are configured to provide electrical continuity to an array of electrode micro-sealing pads 500 disposed along one or both jaw members 280, 282. Commonly-assigned U.S. patent application Ser. No. 10/369,894 shows one example of an open forceps having a plurality of micro sealing pads 500 disposed on opposing electrically conductive surfaces for maintaining the viability of tissue after sealing. The contents of U.S. patent Ser. No. 10/369,894 are hereby incorporated by reference herein.

As disclosed, electrode micro-sealing pads 500 are arranged in a longitudinal, pair-like fashion along the tissue contacting surfaces of jaw members 280, 282. In use, the arrangement of micro-sealing pads 500, across the tissue, only seals the tissue which is between each micro-sealing pad 500 and the opposing jaw members 280, 282. The tissue adjacent each micro-sealing pad 500 remains viable which, as can be appreciated, allows blood and nutrients to flow through the sealed tissue and between the individual tissue welds to promote tissue healing and reduce the possibility of tissue necrosis.

Figure 3:
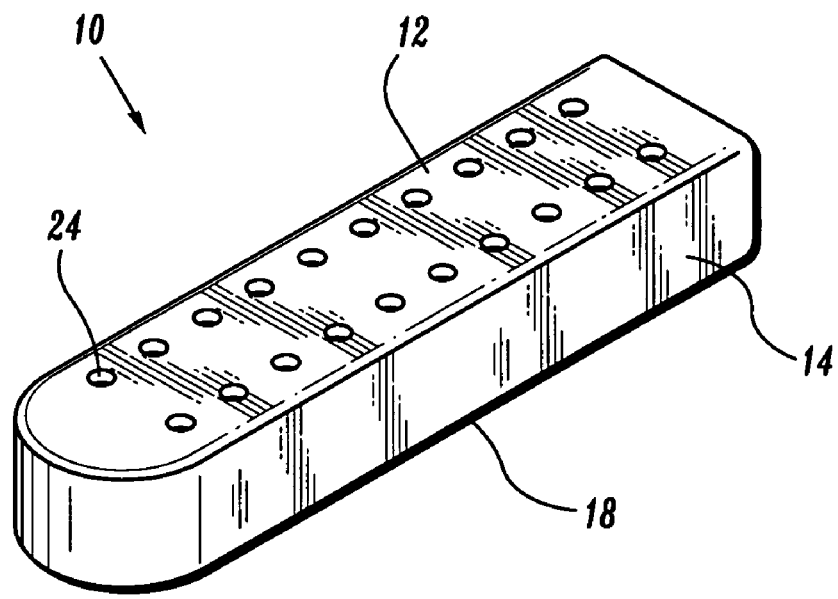
FIG. 3 is a front perspective view of an over shoe in accordance with an embodiment of the present disclosure.
Figure 4:
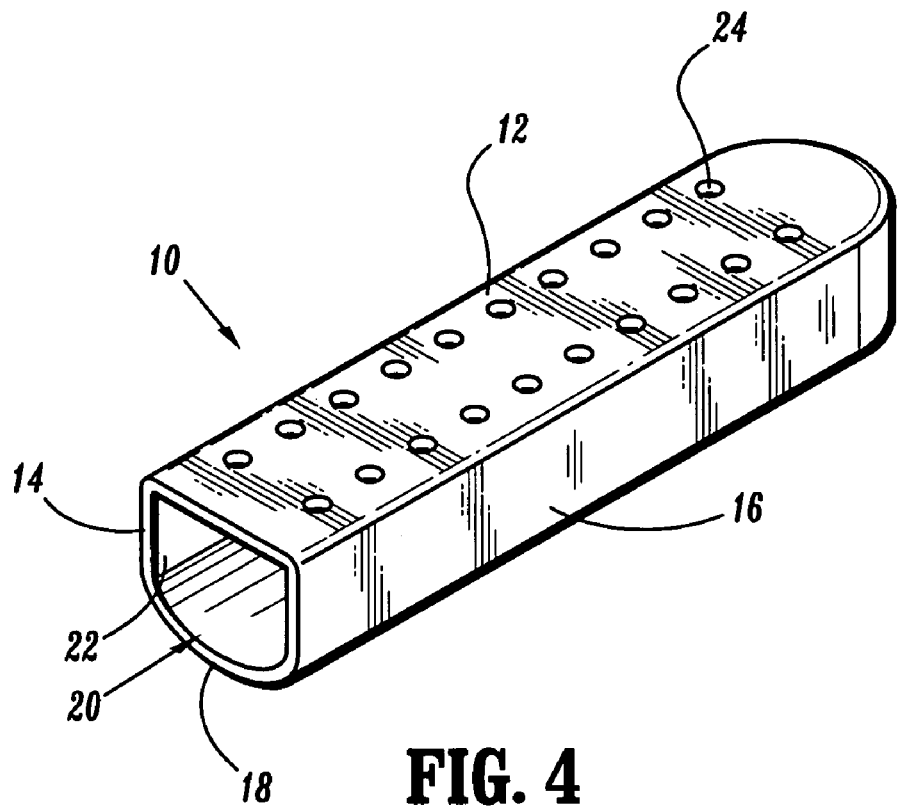
FIG. 4 is a rear perspective view of the over shoe of FIG. 3.

Turning now to FIGS. 3 and 4, an over shoe for operative engagement with at least one of the pair of opposing jaw members 280, 282 of jaw assembly 110 of forceps 100 is shown generally as 10. For the purposes herein, over shoe 10 can be used with either an endoscopic forceps (as depicted in FIGS. 1A and 1B) or an open forceps (as depicted in FIGS. 2A and 2B). Obviously, different geometric considerations apply to use over shoe 10 with each particular type of instrument, however, the novel aspects with respect to over shoe 10 and its operating characteristics remain generally consistent with respect to both open and/or endoscopic forceps.

Over shoe 10 includes a tissue contacting wall 12 and a pair of side walls 14, 16 terminating in an arcuate bottom wall 18. Walls 12-18 of over shoe 10 define a cavity 20 therein sized and dimensioned to receive one of the pair of opposing jaw members 280, 282 therein. Over shoe 10 includes an opening 22 at a proximal end thereof for insertion of one of the pair of opposing jaw members 280, 282 therethrough (i.e., such that over shoe 10 can be "slipped" on over at least one of the pair of opposing jaw members 280, 282).

Over shoe 10 preferably includes a plurality of apertures 24 formed in tissue contacting wall 12 thereof. Preferably, apertures 24, as seen in FIGS. 3 and 4, are arranged in two linear rows, however, any arrangement and/or configuration of apertures 24 is envisioned and contemplated (see FIGS. 12-15), e.g., longitudinally offset rows.

In one embodiment, at least the upper, tissue engaging surface 12 of over shoe 10 is fabricated from a non-conductive material which acts to electrically (and/or thermally) insulate the majority of the tissue engaging wall 12 during activation allowing only a portion of electrosurgical energy through apertures 24. Alternatively and as described in more detail herein, it is also envisioned that the tissue engaging surface 12 may be electrically conductive (and/or thermally conductive or thermally non-conductive) and the apertures 24 non-conductive (and/or the end effector under the over shoe 10 is non-conductive).

Moreover, it is also contemplate that the apertures may vary greatly in size depending upon a particular purpose. For example and as mentioned above, the apertures 24 may be configured in many geometric configurations atop tissue contacting surface 12 which, depending upon the positioning of the apertures and whether the surface 12 is electrically conductive, electrically insulative and/or thermally insulative, will vary the desired tissue effect, e.g., cut, coagulate, blend, seal. In addition to the various geometric parameters which can greatly effect the tissue effect, it is envisioned that the size of the apertures 24 can also play an important role in determining tissue effect. For example, the apertures 24 may be relatively large (from arrange of about 0.001 inches in diameter to about 0.15 inches in diameter (or larger)) for sealing large tissues to maintain viability across the tissue seal as described in commonly owned, U.S. application Ser. No. 10/369,894 the entire contents of which are hereby incorporated by reference herein.

The apertures 24 may also be very small apertures 24 (a diameter in the range of about 0.000394 inches (10 µm) to about 0.0394 inches (1000 µm)) for limiting the current per arc through the tissue surface 12 for creating certain surgical effects as described in commonly-owned, Provisional Application No. 60/432,385 (now U.S. patent application Ser. No. [2879 (203-3439] the entire contents of which are hereby incorporated by reference herein. When the tissue engaging surface 12 is fabricated from non-conductive material, the non-conductive material essentially "pinches" or splits the arc current generated by the electrosurgical generator into a small diameter channel, effectively keeping the same current and voltage, but creating several small arcs from one large arc. Essentially, this has the effect of separating the arc current, effectively increasing the current effect to the tissue, resulting in a finer cut and/or other surgical effect. In other words, the non-conductive material enables a low frequency current to achieve surgical effects and/or results indicative of a high frequency current, while minimizing or preventing thermal damage to adjacent tissue.

As mentioned above, apertures 24 may have a uniform diameter in the range of about 0.000394 inches (10 µm) to about 0.0394 inches (1000 µm). The number of small arcs created from one large arc is inversely proportional to the diameter of apertures 24 formed in tissue contacting wall 12. Preferably, the diameter of each aperture 24 is less than the diameter of the large arc. Hence, when electrosurgical current is applied, for example, to electrode assembly 110 of forceps 100, when over shoe 10 is placed thereon, the arc current is split between apertures 24, thereby controlling or limiting the arc current through each aperture 24. This effect which controls or limits the arc current through each aperture 24 is referred to as "MicroHollow Cathode Discharge" (MCD or MHCD). Commonly owned International Patent Application Serial No. PCT/US03/08146, discloses a porous coating which may be utilized to control arc current, the entire contents being hereby incorporated by reference herein. A large arc area is desired when operating the electrosurgical generator in the coagulation mode while a small arc area is desired when operating the electrosurgical generator in the cut mode.

Moreover, it is envisioned that a series of different over shoes 10 may be sold as a pack to change the desired surgical effect based on size of apertures, geometrical configuration or layout of the apertures for cut, coagulation, sealing, blend, etc.)

In one embodiment, over shoe 10 is made from an insulative material such as ceramic due to its hardness and inherent ability to withstand high temperature fluctuations. Alternatively, over shoe 10 may be made from a material or a combination of materials having a high Comparative Tracking Index (CTI) in the range of about 300 to about 600 volts. Examples of high CTI materials include nylons and syndiotactic polystryrenes such as QUESTRA® manufactured by DOW Chemical. Other materials may also be utilized either alone or in combination, e.g., Nylons, Syndiotacticpolystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

Figure 18A:
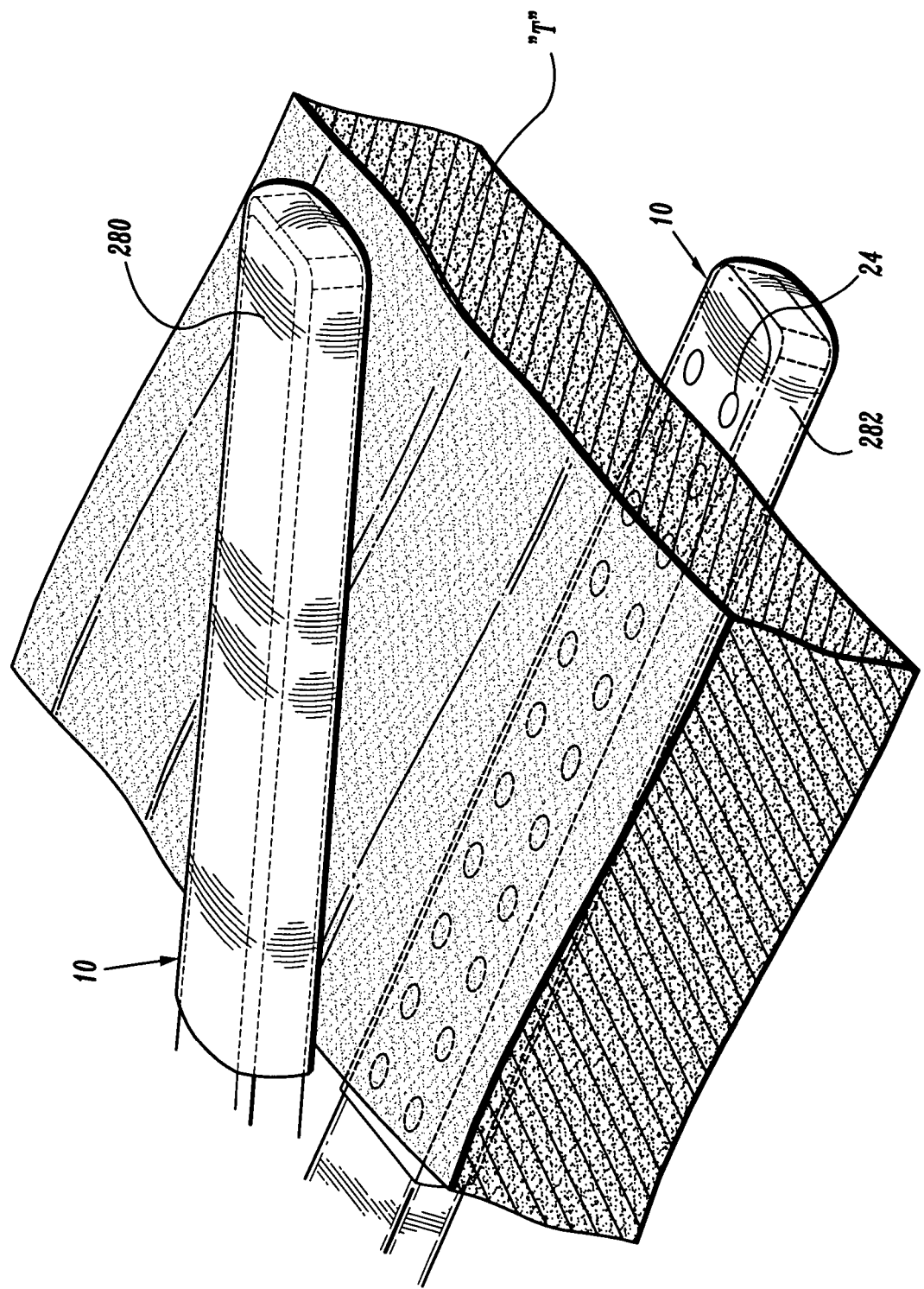
FIG. 18A is a schematic, perspective view of exemplary jaw members approximating tissue including an over shoe, in accordance with the present disclosure, placed on at least one of the jaw members.
Figure 18B:
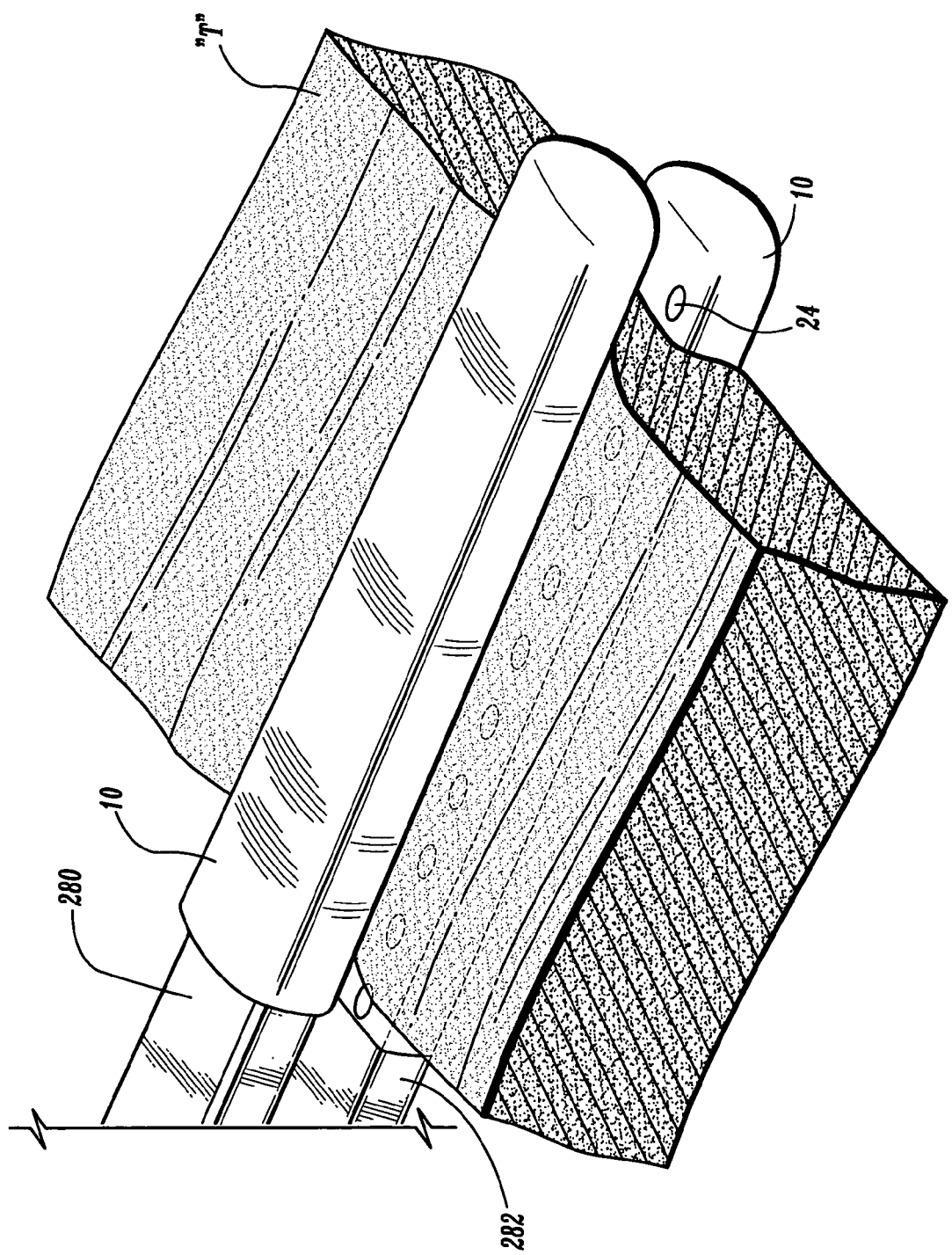
FIG. 18B is a schematic, perspective view of exemplary jaw members grasping tissue including an over shoe, in accordance with the present disclosure, placed on at least one of the jaw members.
Figure 18D:
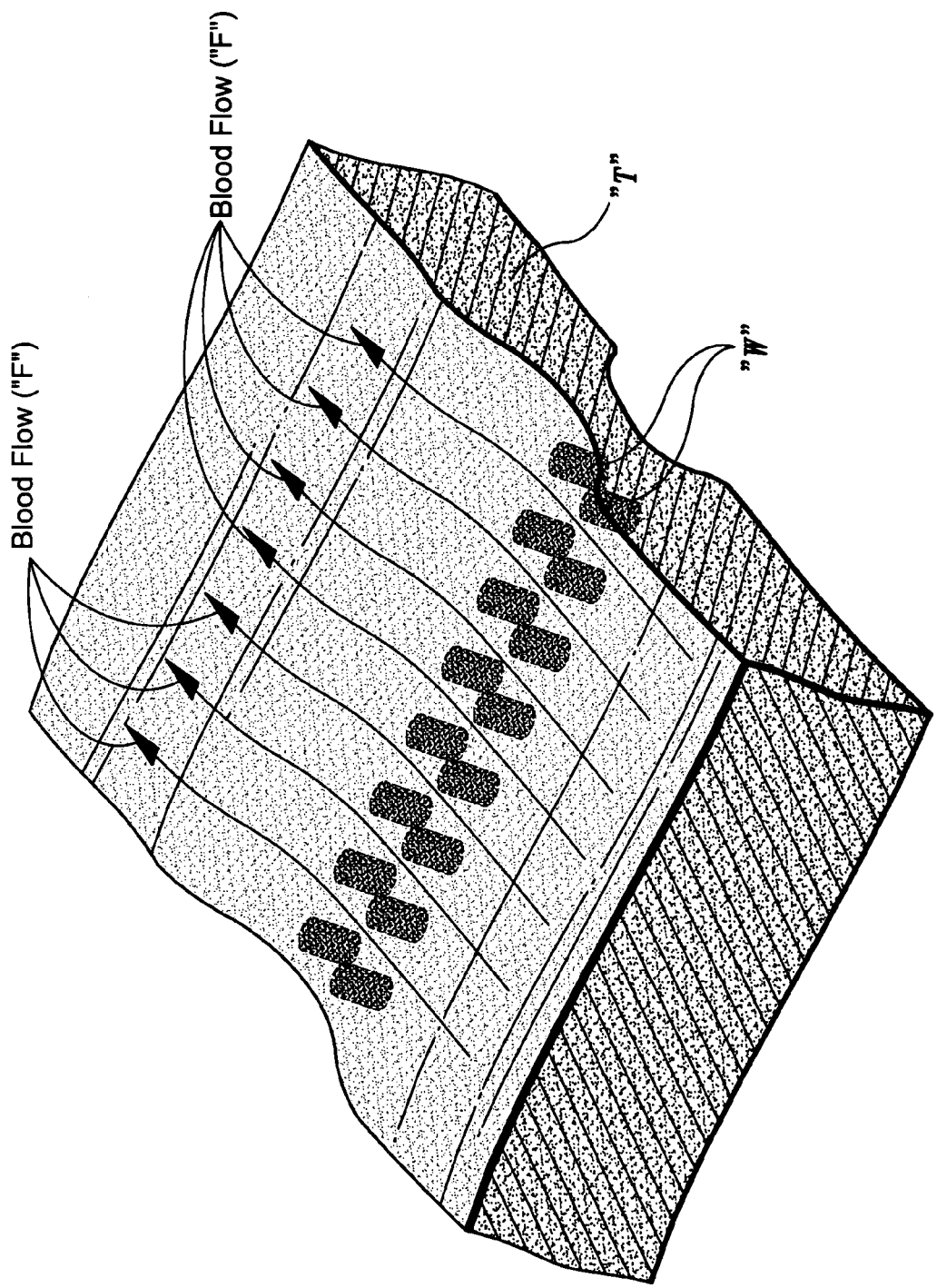
FIG. 18D is a schematic, perspective view showing a series of micro-seals disposed in a pattern across the tissue after activation of the electrode assembly.

The diameter of each of the plurality of apertures 24 can vary in size to produce different surgical effects when operating the electrosurgical generator system in one of several modes, such as, for example, in seal, cut, blend and coagulation modes. In any of these embodiments, the size of the aperture enables the surgeon to control the proportion of tissue vaporization to tissue heating, in order to achieve more controllable and desirable surgical effects. For example, relatively larger apertures 24 (e.g., on the order of about 0.001 inches to about 0.15 inches in diameter (or larger)) are desirable for effecting sealing of relatively large tissue in order to create a micro-sealing pattern across the tissue (see FIG. 18D). Moreover, relatively smaller apertures 24 are desirable for effecting cutting, blending and/or coagulating of relatively smaller tissue. It is envisioned and within the scope of the present disclosure that tissue contacting wall 12 of over shoe 10 can include regions wherein at least one of the regions includes apertures 24 sized to provide one tissue effect, e.g., sealing, and at least one other region includes apertures 24 sized to provide a different surgical effect, e.g., cutting, blending and/or coagulating.

The number of apertures 24 per square centimeter can be uniform or vary along the length of over shoe 10 and/or electrode assembly 110 of forceps 100. The number of apertures 24 per square inch (or per square centimeter) controls the overall treatment area or on a micro scale the arc area. For example, as the number of apertures 24 per square inch (or per square centimeter) increases, the treatment area decreases, and vice-versa. When the tissue surface 12 is electrically conductive, the opposite is true.

Tissue contacting wall 12 of over shoe 10 has a thickness which in turn defines the thickness and/or depth of apertures 24. For a system wherein the apertures are on a micro scale, the thickness of tissue contacting wall 12 controls the system resistance and voltage needed to establish the arc. The thicker tissue contacting wall 12 the greater the system resistance and voltage needed to establish the arc, and vice-versa.

Preferably, tissue contacting wall 12 has a thickness which is predetermined during fabrication of over shoe 10 for effectively operating electrode assembly 110 of forceps 100 in one of several modes, such as seal cut, coagulate and blend, by using the electrosurgical generator. For example, it is envisioned that the tissue contacting wall 12 may have a relatively small thickness, in the range of about 10 μm to about 500 μm, is preferred for operating electrode assembly 110 of forceps 100 in a "cut" mode; tissue contacting wall 12 having a relatively medium thickness, in the range of about 250 μm to about 1 mm, is preferred for operating electrode assembly 110 of forceps 100 in a "blend" mode; and tissue contacting wall 12 having a relatively large thickness, in the range of about 500 μm to 2 mm, is preferred for operating electrode assembly 110 of forceps 100 in the "coagulate" mode.

It is envisioned that the thickness of tissue contacting wall 12 can be varied along the length and/or the width thereof in order to be able to effectively operate electrode assembly 110 of forceps 100 in more than one mode by using the electrosurgical generator at one fixed setting. For example, tissue contacting wall 12 can have a first portion having a first thickness for operating electrode assembly 110 of forceps 100 in one of the seal, cut, blend and coagulate modes and at least one second portion having a second thickness for operating electrode assembly 110 of forceps 100 in another of the seal, cut, blend and coagulate modes.

In one method of use, an over shoe 10 can be placed over each jaw member 280, 282 of forceps 100 or 200, which over shoes 10 are dimensioned in such a manner that may simultaneously effect coagulation between portions of jaw members 280, 282 and effect tissue cutting between other portions of jaw members 280, 282. More particularly, in the areas where tissue contacting walls 12 of over shoes 10 is thicker the tissue held between jaw members 280, 282 will tend to coagulate and in the areas where tissue contacting walls 12 of over shoes 10 is thinner the tissue held between jaw members 280, 282 will tend to be cut. Accordingly, as can be appreciated, a single energy activation of the electrosurgical generator may yield a dual tissue effect which greatly simplifies the coagulating and dividing of tissue.

Similarly, an over shoe may be dimensioned to seal and cut tissue by controlling the thickness of the over shoe along the length or width of each jaw member 280, 282. As can be appreciated, by utilizing a combination of controlling gap distance and sealing pressure and controlling the current to the tissue, a surgeon may simultaneously seal and cut tissue disposed between jaw members 280, 282 due to the unique configuration of the over shoe.

While the insulating type over shoe 10 has been described as being manufactured entirely of a ceramic material, it is envisioned and within the scope of the present disclosure that only tissue contacting wall 12 needs to be manufactured from a ceramic material while the remainder of over shoe 10 (e.g., side walls 14, 16 and bottom wall 18) can be manufactured from some other rigid and/or flexible non-conductive material, such as, for example, plastic, latex, silicone and the like.

Turning now to FIGS. 5-9, an over shoe in accordance with another embodiment of the present disclosure is shown generally as 10a. Over shoe 10a is substantially similar to over shoe 10 and will be discussed in detail to the extent necessary to identify differences in construction and operation. As seen in FIGS. 5-9 bottom wall 18 includes a longitudinally oriented slot 30 extending substantially the entire length of over shoe 10a. Accordingly, slot 30 enables over shoe 10a to be slipped over and onto, for example, jaw members 280, 282, having widths which are larger than the width of tissue contacting wall 12 and/or larger than the width of opening 22 formed at the proximal end thereof. In other words, as seen in FIGS. 8 and 9, slot 30 enables and/or allows side walls 14, 16 to deflect and/or bow orthogonally outward (as indicated by arrows "A") when a jaw member 280, 282 is inserted into over shoe 10a.

Tuning now to FIG. 10, an over shoe, in accordance with yet another embodiment of the present disclosure, is shown generally as 10b. Over shoe 10b is substantially similar to over shoe 10 and will only be discussed in detail to the extent necessary to identify differences in construction and operation. As seen in FIG. 10, over shoe 10b includes at least one, preferably a pair of bands 32 secured to and extending across tissue contacting wall 12. Preferably, bands 32 are elastic and enable over shoe 10b to be slipped onto and/or into engagement with jaw members 280, 282 of varying width and/or thickness. While elastic bands 32 are preferred, it is envisioned and within the scope of the present disclosure for bands 32 to be inelastic, capable of being tied to one another and/or capable of being releasably secured to one another (e.g., hook and loop type fasteners).

Turning now to FIG. 11, an exemplary positioning arrangement for the engagement of over shoe 10 to a jaw member 280, 282 of forceps 100 or 200, is shown. As seen in FIG. 11, the inner surface of one, preferably each side wall 14, 16 of over shoe 10 includes a nub, projection or the like 34 extending therefrom. Nubs 34 preferably engage with and/or are received in corresponding recesses 283 formed in the side surfaces of jaw members 280, 282, in a snap-fit type engagement. In this manner, when over shoe 10 is slipped onto and/or over one of jaw members 280, 282 of forceps 100 or 200, the positioning arrangement fixes the location and/or position of the apertures (not shown) on jaw member 280 or 282. Meanwhile, when over shoe 10 is slipped onto and/or over the other of jaw members 280, 282 of forceps 100 or 200, the positioning arrangement fixes the location and/or position of the apertures (not shown) on the other of jaw member 280 or 282. In this manner, the position of the apertures (not shown) on jaw member 280 can be fixed and predetermined relative to the position of the apertures (not shown) on jaw member 282. For example, apertures 24 of over shoe 10 corresponding to jaw member 280 can be in juxtaposed vertical registration or in juxtaposed offset registration with apertures 24 of over shoe 10 corresponding to jaw member 282 depending on a particular purpose.

As best seen in FIG. 11, various electrical connections of electrode assemblies 110, 210 (not shown) are configured to provide electrical continuity to a series of electrode pads 290 disposed atop at least one of jaw members 280, 282 for transmitting electrosurgical energy to the tissue. When the over shoe 10 is electrically conductive, different electrical connections would obviously apply.

Turning now to FIGS. 12-15, exemplary illustrations of various arrangements and patterns of apertures 24, formed in tissue contacting wall 12, are shown for use with either an electrically conductive overshoe or an electrically insulative over shoe. As seen in FIG. 12, apertures 24 are unevenly distributed and/or formed in tissue contacting wall 12. In particular, there is shown an increased density of apertures 24 formed in both a distal region and a proximal region of tissue contacting wall 12 and a reduced density of apertures 24 formed in a central region of tissue contacting wall 12.

As seen in FIG. 13, tissue contacting wall 12 of over shoe 10 can be provided with at least two longitudinally oriented rows of alternatingly-sized apertures, namely, relatively larger sized apertures 24a and relatively smaller sized apertures 24b.

As seen in FIG. 14, tissue contacting wall 12 of over shoe 10 can be provided with at least two longitudinally-oriented, preferably offset, rows of elongate slots 24c formed therein.

As seen in FIG. 15, slots 24c can be oriented at an angle with respect to a longitudinal axis of tissue contacting wall 12.

While FIGS. 12-15 illustrate exemplary arrangements and/or patterns of apertures that can be formed in tissue contacting wall 12 of over shoe 10, in no way is this to be an exhaustive illustration of all of the arrangements and/or patterns that can be formed in tissue contacting wall 12. For example, any of the arrangements and/or patterns illustrated in FIGS. 12-15 can be interchanged and/or combined with one another in any order, orientation and/or density.

Figure 16:
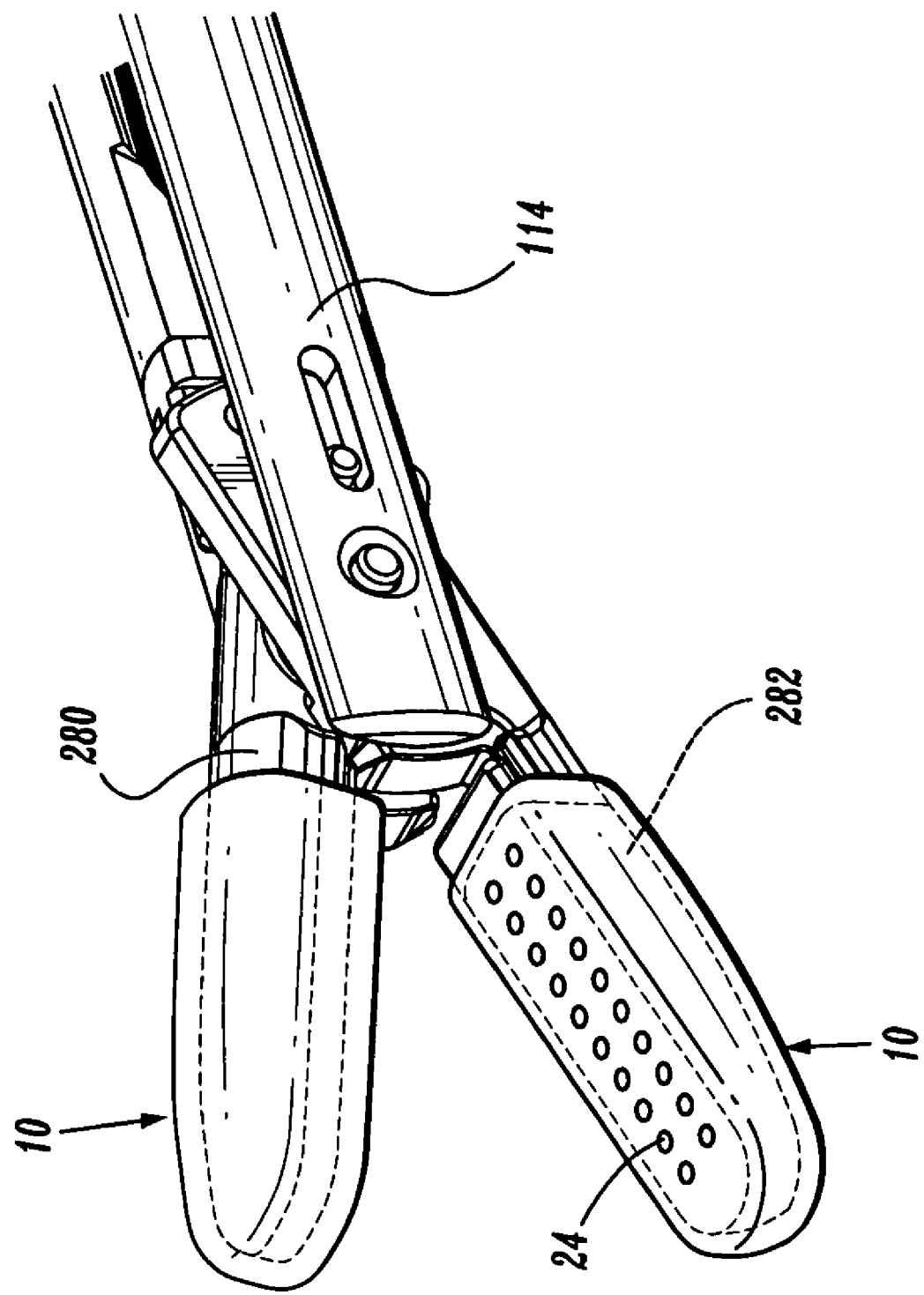
FIG. 16 is an enlarged perspective view of the jaw assembly of the endoscopic forceps of FIG. 1A, illustrating the placement of an over shoe, in accordance with the present disclosure, thereon.
Figure 17:
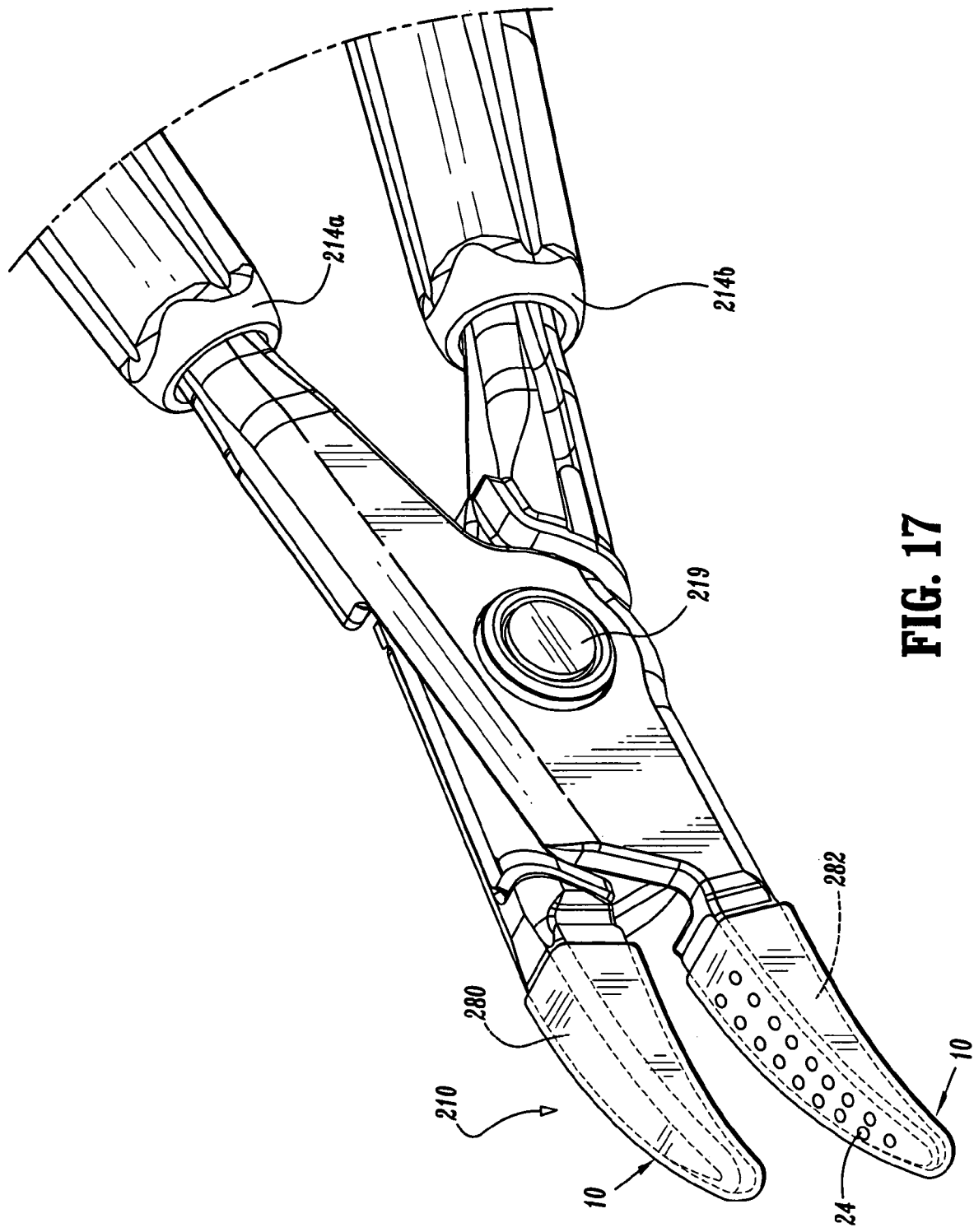
FIG. 17 is an enlarged perspective view of the jaw assembly of the endoscopic forceps of FIG. 2A, illustrating the placement of an over shoe, in accordance with the present disclosure, thereon.

As seen in FIG. 16, over shoes 10, configured and dimensioned to be slipped over jaw members 280, 282 of forceps 100, are shown in position over each jaw member 280, 282 thereof. As seen in FIG. 17, over shoes 10, configured and dimensioned to be slipped over jaw members 280, 282 of forceps 200, are shown in position over each jaw member 280, 282 thereof.

Although the majority of the figure drawings depict an over shoe for use with a bipolar forceps for use in connection with endoscopic surgical procedures, over shoes for open forceps are also contemplated for use in connection with traditional open surgical procedures.

In use, as depicted in the insulating embodiment of FIGS. 18A-18D, over shoe 10 positioned on at least one of jaw members 280, 282, the surgeon initially approximates tissue "T" (see FIG. 18A) between the opposing jaw members 280, 282 and then grasps tissue "T" (see FIG. 18B) by manipulating forceps 100 or 200 to approximate jaw members 280, 282 towards one another. Once tissue "T" is grasped, the surgeon selectively activates electrosurgical generator (see FIG. 18C) to supply electrosurgical energy to electrode pad 290 of each jaw member 280, 282. In particular, electrosurgical energy flows from the positive terminal of electrosurgical generator, to electrode pad 290 of jaw member 282, through aperture 24 of over shoe 10 placed on jaw member 282, through tissue "T", through aperture 24 of over shoe 10 placed on jaw member 280, to electrode pad 290 of jaw member 280, and back to the negative terminal of electrosurgical generator. As a result thereof, an intermittent pattern of tissue seals and/or welds "W" are created along tissue "T" (see FIGS. 18C and 18D).

The arrangement and/or pattern of apertures 24 formed in over shoes 10 only permits the sealing and/or welding of tissue "T" which is located between juxtaposed apertures 24 of over shoes 10 placed on each jaw member 280, 282. Tissue "T" adjacent each aperture 24 remains viable which, as can be appreciated, allows blood and nutrients to flow through the sealed tissue "T" and between the individual tissue welds "W", as indicated by arrows "F" of FIG. 18D, to promote tissue healing and reduce the chances of tissue necrosis. As mentioned above, a conductive over shoe 10 may be used to obtain a similar surgical result.

A controller "C" (see FIG. 18C) may be electrically interposed between electrosurgical generator and electrode pads 290 to regulate the electrosurgical energy supplied thereto depending upon certain electrical parameters, such as, for example, current impedance, temperature, voltage, tissue type, tissue thickness, etc. For example, the forceps or controller "C" may include one or more sensors and/or smart sensors (not shown) which communicate with electrosurgical generator (or with a smart circuit, a computer, a feedback loop, etc.) to automatically regulate the electrosurgical intensity (e.g., waveform, current, voltage, etc.) to enhance the sealing and/or welding process. The sensors may measure or monitor one or more of the following parameters: tissue temperature, tissue impedance at the weld site, the change in impedance of the tissue over time and/or changes in power or current applied in the tissue over time. An audible or visual feedback monitor (not shown) may be employed to convey to the surgeon regarding the overall seal quality of the completion of an effective tissue seal.

Moreover, a PCB (printed circuit board) circuit or flex circuit (not shown) may be utilized to provide information relating to the gap distance (e.g., with a proximity detector) between jaw members 280, 282, the sealing pressure between jaw members 280, 282 prior to and during activation, load (e.g., with a strain gauge), the thickness of tissue "T" prior to or during activation, the impedance across the tissue during activation, and the rate of tissue expansion during activation and sealing.

Several examples of such devices and systems are described in commonly-owned U.S. application Ser. No. 10/427,832 the entire contents of which are hereby incorporated by reference herein. Methods and systems for adjusting and setting the gap distance are also disclosed in commonly assigned U.S. Provisional Patent Application Ser. No. 60/470,632, the entire contents also being hereby incorporated by reference herein. Methods and systems for controlling the output of RF medical generators are disclosed in commonly assigned U.S. patent application Ser. No. 10/417,823, the entire contents being hereby incorporated by reference herein.

It is envisioned that the PCB circuit may be designed to provide electrical feedback to electrosurgical generator relating to one or more of the above parameters either on a continuous basis or upon inquiry from electrosurgical generator. For example, a PCB circuit may be employed to control the power, current and/or type of current waveform delivered from electrosurgical generator to jaw members 280, 282 in order to reduce collateral damage to surrounding tissue during activation, e.g., thermal spread, tissue vaporization and/or steam from the treatment site. Examples of various control circuits, generators and algorithms which may be utilized are disclosed in U.S. Pat. No. 6,228,080 and U.S. patent application Ser. No. 10/073,761, the entire contents of both of which are hereby incorporated by reference herein.

From the foregoing and with reference to the various figure drawings, those skilled in the art will appreciate that certain modifications can also be made to the present disclosure without departing from the scope of the same. For example, it is envisioned that the diameter of the apertures of the over shoe may be varied during the manufacturing process of the over shoe according to the type of surgical instrument to be used. In particular, it is envisioned that one sized aperture diameter may be used for electrosurgical blades for coagulating or cutting tissue while another aperture diameter may be used for electrosurgical forceps which utilize a combination of closing force, gap distance between jaw members and amount of electrosurgical energy, to seal tissue.

Moreover, it is envisioned that the number of apertures per square inch (or per square centimeter) may be modified during the manufacturing process to control the treatment area and minimize the collateral effect to surrounding tissue. In addition, as discussed above, the shape of the apertures include and are not limited to circular, triangular, rectangular, oval and the like. It is also contemplated that the thickness of the tissue contacting wall 12 of the over shoe 10 may be modified during the manufacturing process to establish a preferred resistance and voltage for creating a desired surgical effect.

Figure 19A:
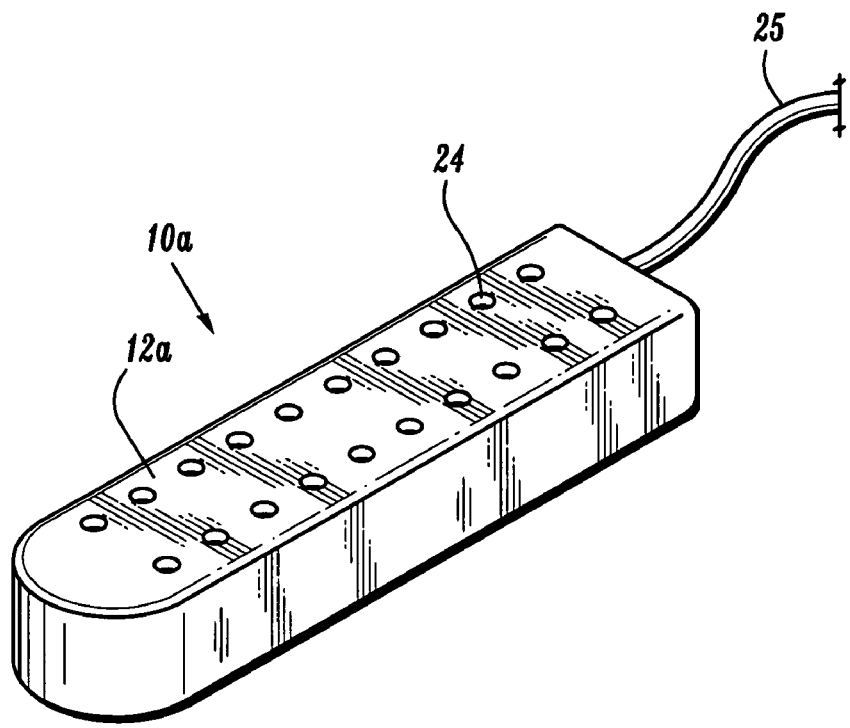
FIG. 19A is a schematic, perspective view of an alternate embodiment of the present disclosure showing a conductive over shoe.

As mentioned repeatedly above, it is further envisioned that the jaw members 280, 282 of forceps 100 can be insulative and that an over shoe 10, or preferably, tissue contacting wall 12 of over shoe 10, is fabricated from a conductive material and electrically connected to an electrosurgical energy source (See FIG. 19A). In this manner, any non-electrosurgical forceps can be retrofitted with over shoe 10 placed on or slipped over at least one of its jaw members. Apertures 24 of over shoe 10 in turn act as cooling spots (i.e., regions where limited electrosurgical energy or thermal energy is transmitted). In this manner, following use and application of electrosurgical energy to tissue "T", the regions where over shoe 10 contacts tissue "T" is where tissue sealing and/or welding occurs and the regions where apertures 24 are located do not experience tissue sealing and/or welding and remain viable tissue. As can be appreciated, each over shoe would be attachable to a different electrical potential emanating from an electrosurgical generator such that the over shoes are capable of conducting bipolar electrosurgical energy through tissue held therebetween. As such, wires or conductive elements 25 would be used to accomplish this purpose.

Figure 19B:
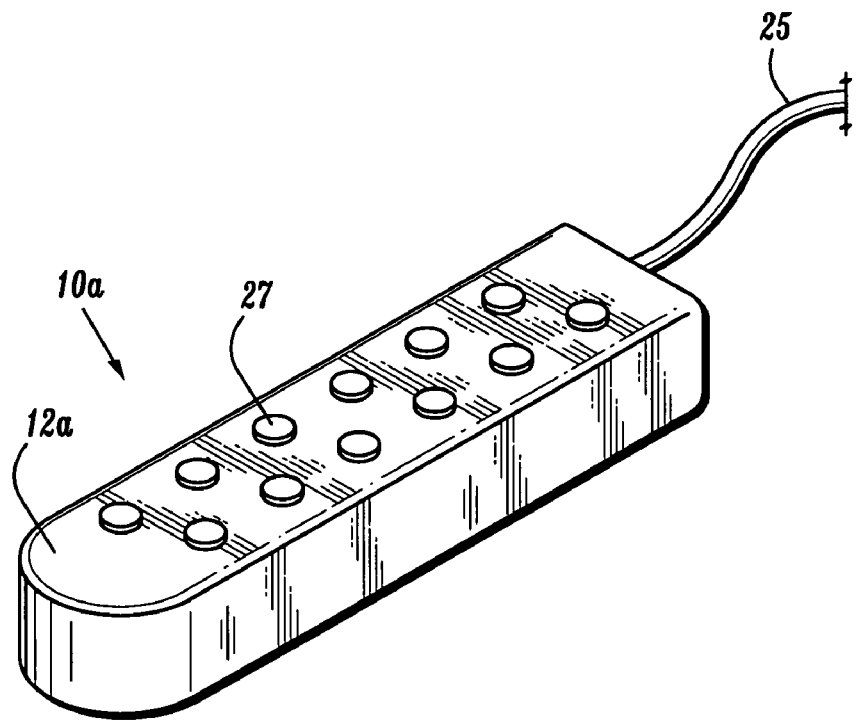
FIG. 19B is a schematic, perspective view of another alternate embodiment of the present disclosure showing a conductive over shoe with raised conductive projections.

As best seen in FIG. 19B, it is also contemplated that over shoe 10 can include electrically conductive tissue contacting portions 27 or projections in lieu of apertures 24. For example, tissue contacting wall 12a and/or electrically conductive tissue contacting portions 27 may be arranged on surface 12a to project therefrom to create a pattern of tissue welds for treating tissue. It is also envisioned that the projections 27 can be coated with non-stick materials. When utilized on these surfaces, the non-stick materials provide an optimal surface energy for eliminating sticking due in part to the surface texture and the susceptibility to surface breakdown due to electrical effects and corrosion in the presence of biologic tissues. As can be appreciated, reducing the amount that the tissue "sticks" during sealing improves the overall efficacy of the instrument.

The non-stick materials may be manufactured from one (or a combination of one or more) of the following "non-stick" materials, namely, nickel-chrome, chromium nitride, Med-Coat 2000 manufactured by The Electrolizing Corporation of OHIO, Inconel 600 and tin-nickel. Inconel 600 is a so-called "super alloy" which is manufactured by Special Metals, Inc. located in Conroe Tex. Super alloys are primarily used in environments which require resistance to corrosion and heat. The high Nickel content of Inconel 600 makes the material especially resistant to organic corrosion. As can be appreciated, these properties are desirable for bipolar electrosurgical instruments which are naturally exposed to high temperatures, high RF energy and organic matter.

One particular class of materials disclosed herein has demonstrated superior non-stick properties and, in some instances, superior micro-seal quality. For example, nitride coatings which include, but are not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reduce overall sticking. For example, high nickel/chrome alloys with a Ni/Cr ratio of approximately 5:1 have been found to significantly reduce sticking in bipolar instrumentation.

While the above disclosure and figures relate to hemostats, forceps or bipolar instruments, it is contemplated and within the scope of the present disclosure that the over shoes disclosed herein can be used in connection with and/or association with electrosurgical pencils and the like.

Although the present disclosure has been described with respect to particular embodiments, it will be readily apparent to those having ordinary skill in the art to which it pertains, that changes and modifications may be made thereto without departing from the spirit or scope of the disclosure.

What is claimed is:

1. An electrosurgical instrument comprising:
   a pair of juxtaposed jaw members pivotably associated with one another, at least one of which includes an electrically conductive surface disposed thereon in electrical communication with an electrosurgical energy source;
   a selectively engageable over shoe adapted to engage the electrically conductive surface, the overshoe including:
   a tissue contacting wall configured and dimensioned to selectively and substantially overlie the electrically conductive surface of the electrosurgical instrument, the tissue contacting wall including a plurality of apertures formed therethrough configured to allow current therethrough, the tissue contacting wall being fabricated from a non-conductive material.

2. The electrosurgical instrument according to claim 1, wherein the tissue contacting wall is fabricated from a ceramic material.

3. The over shoe according to claim 2, wherein the tissue contacting wall includes a plurality of apertures are arranged in pairs along a length of the electrically conductive surface.

4. The over shoe according to claim 3, wherein the apertures are evenly sized.

5. The over shoe according to claim 3, wherein the apertures are generally circular.

6. The over shoe according to claim 5, wherein the apertures have a diameter of about 10 µm to about 1000 µm.

7. The over shoe according to claim 3, wherein the apertures are elongated slots.

8. The over shoe according to claim 7, wherein the elongated slots are in at least one of a parallel orientation with respect to the longitudinal axis and at an angle with respect to the longitudinal axis.

9. The over shoe according to claim 2, wherein the apertures are randomly arranged.

10. The electrosuraical instrument according to claim 2, further comprising a pair of side walls extending from lateral side edges of the tissue contacting wall, and a bottom wall interconnecting the pair of side walls, the tissue contacting wall, the bottom wall and the side walls defining a cavity configured and dimensioned to substantially receive a jaw member of the electrosurgical instrument.

11. The over shoe according to claim 10, wherein the bottom wall includes a longitudinally oriented slot running along a length thereof which promotes friction fit engagement between the over shoe and the jaw member.

12. The over shoe according to claim 10, further comprising at least one inter-engaging member extending from an inner surface of at least one of the pair of side walls, the at least one inter-engaging member being configured and dimensioned to engage a complementary recess formed in the jaw member.

13. The over shoe according to claim 12, wherein the at least one inter-engaging member registers the apertures of an over shoe placed on one of the pair of jaw members relative to the apertures of an over shoe placed on the other of the other of the pair of jaw members.

14. The over shoe according to claim 13, wherein the apertures are in vertical registration relative to one another.

15. The overshoe according to claim 13, wherein the apertures are offset relative to one another.

16. The over shoe according to claim 2, further comprising at least one band extending between and engaged with each side terminal edge of the tissue contacting wall.

17. The electrosurciical instrument according to claim 2, wherein the tissue contacting wall has a thickness in the range of about 10 μm to about 2 mm.

18. The over shoe according to claim 17, wherein the thickness of the tissue contacting wall is non-uniform.

19. The electrosurgical instrument according to claim 1, wherein the over shoe has a plurality of apertures disposed therethrough.

20. The electrosurgical instrument according to claim 19, wherein the apertures are configured based on a particular surgical purpose, the surgical purpose being selected from the group consisting of cuffing, coagulating, sealing, dissecting, and blending.

21. An electrosurgical instrument capable of performing tissue sealing, the electrosurgical instrument comprising:

a selectively engageable overshoe adapted to engage an electrically conductive surface on the electrosurgical instrument, the overshoe including:

a tissue contacting wall fabricated from a non-conductive material, the tissue contacting wall being configured and dimensioned to over lie the electrically conductive surface disposed on the electrosurgical instrument, the tissue contacting wall including at least two apertures extending therethrough configured to allow current therethrough.

22. The electrosurgical instrument according to claim 21, wherein the tissue contacting wall is fabricated from materials having a high Comparative Tracking Index.

23. The electrosurgical instrument according to claim 22, wherein the Comparative Tracking Index is in the range of about 300 to about 600 volts.

24. The electrosurgical instrument according to claim 21, wherein the tissue contacting wall is fabricated from a group consisting of at least one of nylons, syndiotactic polystryrenes, polybutylene terephthalate, polycarbonate, acrylonitrile butadiene styrene, polyphthalamide, polymide, polyethylene terephthalate, polyamide-imide, acrylic, polystyrene, polyether sulfone, aliphatic polyketone, acetal copolymer, polyurethane, nylon with polyphenylene-oxide dispersion, and acrylonitrile styrene acrylate.

25. The electrosurgical instrument according to claim 24, wherein the apertures are configured based on a particular surgical purpose, the surgical purpose being selected from the group consisting of cutting, coagulating, sealing, dissecting, and blending.

* * * * *

UNITED STATES PATENT AND TRADEMARK OFFICE
CERTIFICATE OF CORRECTION

PATENT NO. : 7,442,193 B2  
APPLICATION NO. : 10/718379  
DATED : October 28, 2008  
INVENTOR(S) : Shields et al.

Page 1 of 1

It is certified that error appears in the above-identified patent and that said Letters Patent is hereby corrected as shown below:

Column 14, In Claim 1, line 9, please delete "overshoe" and insert --over shoe--.
Column 14, In Claim 3, line 20, please delete "over shoe" and insert --electrosurgical instrument--.
Column 14, In Claim 4, line 23, please delete "over shoe" and insert --electrosurgical instrument--.
Column 14, In Claim 5, line 25, please delete "over shoe" and insert --electrosurgical instrument--.
Column 14, In Claim 6, line 27, please delete "over shoe" and insert --electrosurgical instrument--.
Column 14, In Claim 7, line 29, please delete "over shoe" and insert --electrosurgical instrument--.
Column 14, In Claim 8, line 31, please delete "over shoe" and insert --electrosurgical instrument--.
Column 14, In Claim 9, line 35, please delete "over shoe" and insert --electrosurgical instrument--.
Column 14, In Claim 11 line 44, please delete "over shoe" and insert --electrosurgical instrument--.
Column 14, In Claim 12, line 48, please delete "over shoe" and insert --electrosurgical instrument--.
Column 14, In Claim 13, line 54, please delete "over shoe" and insert --electrosurgical instrument--.
Column 14, In Claim 13, line 55, please delete "an" and insert --the--.
Column 14, In Claim 13, line 57, please delete "an over shoe placed on the other of the other" and insert --another over shoe placed on the other one--.
Column 14, In Claim 14, line 59, please delete "over shoe" and insert --electrosurgical instrument--.
Column 14, In Claim 15, line 61, please delete "overshoe" and insert --electrosurgical instrument--.
Column 14, In Claim 16, line 63, please delete "over shoe" and insert --electrosurgical instrument--.
Column 15, In Claim 18, line 4, please delete "over shoe" and insert --electrosurgical instrument--.
Column 15, In Claim 21, line 18, please delete "overshoe" and insert --over shoe--.

Signed and Sealed this  
First Day of March, 2011

David J. Kappos  
*Director of the United States Patent and Trademark Office*